US008012947B2

(12) United States Patent
Tomic et al.

(10) Patent No.: US 8,012,947 B2
(45) Date of Patent: Sep. 6, 2011

(54) METHODS AND COMPOSITIONS FOR PROMOTING WOUND HEALING

(75) Inventors: Marjana Tomic, Hillsdale, NJ (US); Carl Peter Blobel, Eastchester, NY (US); Asheesh Harsha, New York, NY (US)

(73) Assignee: Hospital for Special Surgery, New York, NY (US)

( * ) Notice: Subject to any disclaimer, the term of this patent is extended or adjusted under 35 U.S.C. 154(b) by 333 days.

(21) Appl. No.: 12/047,106

(22) Filed: Mar. 12, 2008

(65) Prior Publication Data

US 2009/0068251 A1 Mar. 12, 2009

Related U.S. Application Data

(60) Provisional application No. 60/918,367, filed on Mar. 15, 2007.

(51) Int. Cl.
*A61K 31/70* (2006.01)
*A61K 39/395* (2006.01)
*C07H 21/02* (2006.01)
*C07H 21/04* (2006.01)
*C12Q 1/68* (2006.01)

(52) U.S. Cl. ............. 514/44 A; 536/23.1; 536/24.1; 536/24.5; 424/130.1; 435/6; 435/377

(58) Field of Classification Search .......... None
See application file for complete search history.

(56) References Cited

U.S. PATENT DOCUMENTS 5,773,438 A * 6/1998 Levy et al. ............ 514/237.8
6,492,422 B2 * 12/2002 O'Brien et al. ............ 514/562
2004/0002467 A1 1/2004 Ward et al.

FOREIGN PATENT DOCUMENTS
WO WO 97/40072 10/1997

OTHER PUBLICATIONS

Harsha et al. J. Mol. Med. vol. 86:961-969, 2008.*
Asakura, M. et al., 2002, "Cardiac hypertrophy is inhibited by antagonism of ADAM12 processing of HB-EGF: Metalloproteinase inhibitors as a new therapy," Nat. Med. 8(1):35-40.
Blobel, C. P., 1997,"Metalloprotease-Disintegrins: Links to Cell Adhesion and Cleavage of TNFα and Notch," Cell, 90:589-592.
Blobel, C. P., 2005, "Adams: Key Components in EGFR Signalling and Development," Nat Rev Mol Cell Biol. 6(1):32-43.
Brem, H. et al., 2007, "Molecular Markers in Patients with Chronic Wounds to Guide Surgical Debridement," Mol Med. Jan.-Feb.;13(1-2):30-9.
Cao, Y. et al., 2001, Metalloprotease-disintegrin ADAM 12 interacts with α-actinin-1, Biochem. J. 357:353 361.
Clark, A., 1993, "Biology of Dermal Wound Repair," Dermatol. Clin. 11(4):657 666.
Currie, C. et al., 1998, "The Epidemiology and Cost of Inpatient Care for Peripheral Vascular Disease, Infection, Neuropathy, and Ulceration in Diabetes," Diabetes Care 21(1):42-48.
Evans, J. 2001,"Fertilin β and other ADAMs as integrin ligands: insights into cell adhesion and fertilization," BioEssays 23:628-639.
Falanga, V. et al., 1992, "Topical Use of Human Recombinant Epidermal Growth Factor (h-EGF) in Venous Ulcers," J. Dermatol. Surg. Oncol. 18:604 606.
Freedberg, I. et al., 2001, "The Keratins and the Keratinocyte Activation Cycle," J. of Investigative Dermatology, 116(5) 633-640.
Galliano, M. et al., 2000, "Binding of ADAM12, a Marker of Skeletal Muscle Regeneration, to the Muscle-specific Actin-binding Protein, α-Actinin-2, Is Required for Myoblast Fusion." J. Biol. Chem. 275:13933-13939.
Gentzkow, G. et al., 1996, "Use of Dermagraft, a Cultured Human Dermis, to Treat Diabetic Foot Ulcers ," Diabetes Care 19(4):350-354.
Gilpin, B. et al., 1998, A Novel, Secreted Form of Human ADAM 12 (Meltrin α) Provokes Myogenesis in Vivo, J. Biol. Chem. 273:157 166.
Gordois, A. et al., 2003, "The Health Care Costs of Diabetic Peripheral Neuropathy in the U.S.," Diabetes Care 26(6):1790-1795.
Gough, A. et al., 1997, "Randomised placebo-controlled trial of granulocyte-colony stimulating factor in diabetic foot infection," Lancet 350:855-859.
Harris, H. et al., 1997, "Expression of Meltrin-α mRNA is not Restricted to Fusagenic Cells," J. Cell. Biochem. 67:136 142.
Iba, K. et al., 1999, Cysteine-Rich Domain of Human ADAM 12 (Meltrin α) Supports Tumor Cell Adhesion, Am. J. Pathol. 154:1489 1501.
Inoue, D. et al., 1998, "Cloning and Initial Characterization of Mouse Meltrin β and Analysis of the Expression of Four Metalloprotease Disintegrins in Bone Cells," J. Biol. Chem. 273(7):4180-4187.
Kadota, N. et al,. 2000, "Endogenous Meltrin α is Ubiquitously Expressed and Associated with the Plasma Membrane but Exogenous Meltrin α Is Retained in the Endoplasmic Reticulum," Biochem. 128(6):941 949.
Kang, Q. et al., 2000, "Metalloprotease-disintegrin ADAM 12 binds to the SH3 domain of Src and activates Src tyrosine kinase in C2C12 cells," J. Biol. Chem. 352: 883-892.
Kang, Q. et al., 2001, "Direct Interaction between the Cytoplasmic Tail of ADAM 12 and the Src Homology 3 Domain of p85α Activates Phosphatidylinositol 3-Kinase in C2C12 Cells," Biochem. J. 276(27): 24466-24472.
Kirsner, R. 2005, "The Science of Bilayered Cell Therapy," Supplement to Wounds, Sep. 6-16.
Kurisaki, T. et al., 2003, "Phenotypic Analysis of Meltrin α (ADAM12)-Deficient Mice: Involvement of Meltrin α in Adipogenesis and Myogenesis," Mol. Cell. Biol. 23 (1): 55-61.
Kurisaki, T. et al., 1998, "Spatially- and temporally-restricted expression of meltrin α (ADAM12) and β (ADAM19) in mouse embryo," Mech. Dev. 73:211-215.

(Continued)

Primary Examiner — Sean McGarry
(74) Attorney, Agent, or Firm — Dechert LLP

(57) ABSTRACT

Provided herein are compositions and methods that inhibit expression of Adam12 gene products, such as ADAM12 mRNA and/or ADAM12 polypeptides, as a therapeutic approach for the treatment of, or promotion of healing of, wounds.

13 Claims, 13 Drawing Sheets

OTHER PUBLICATIONS

Kveiborg, M. et al., 2005, "A Role for ADAM12 in Breast Tumor Progression and Stromal Cell Apoptosis," *Cancer Res.*, 65(11):4754-4761.

Loechel, F. et al., 1998, "Human ADAM 12 (Meltrin α) is an Active Metalloprotease," *J. Biol. Chem.* 273(27):16993-16997.

Loechel, F. et al., 1999, Regulation of Human ADAM 12 Protease by the Prodomain: Evidence for a Functional Cysteine Switch, *J. Biol. Chem.* 274(19):13427-13433.

Mahajan, M. et al., 2004, "The Nuclear Hormone Receptor Coactivator NRC Is a Pleiotropic Modulator Affecting Growth, Development, Apoptosis, Reproduction, and Wound Repair," *Mol. Cell. Biol.* 24(11): 4994-5004.

Martin, P., 1997, "Wound Healing-Aiming for Perfect Skin Regeneration," *Science*, 276:75-81.

Mauch, C. et al., 1994, "Role of the extracellular matrix in the degradation of connective tissue," *Arch. Dermatol. Res.* 287:107 114.

Mauro, T. M., 1992, "Autologous Skin Grafts for Leg Ulcers," *West J Med.* 156(2): 191.

Morasso, M. et al., 2005, "Epidermal Stem Cells: The Cradle of Epidermal Determintaion, Differentiation and Wound Healing," *Biol Cell*, 97:173-183.

Peduto, L. et al., 2006, "ADAM12 is highly expressed in carcinoma-associated stroma and is required for mouse prostate tumor progression," *Oncogene*, 25:5462-5466.

Primakoff, P. et al., 2000, "The ADAM Gene Family: Surface Proteins with Adhesion and Protease Activity," *Trends Genet* 16(2):83-87.

Rees, R. et al., 1997, "Becaplermin gel in the treatment of pressure ulcers: a phase II randomized, double-blind, placebo-controlled study ," *Wound Repair Regen.* 7:141 147.

Reiber, G., 1992, "Diabetic Foot Care-Financial Implications and Practice Guidelines," *Diabetes Care* 15(suppl. 1):29-31.

Robson, M. et al., 1992, "The Safety and Effect of Topically Applied Recombinant Basic Fibroblast Growth Factor on the Healing of Chronic Pressure Sores," *Ann. Surg.* 216(40):401 408.

Shi, Z. et al., 2000, "ADAM 12, a Disintegrin Metalloprotease, Interacts with Insulin-like Growth Factor-binding Protein-3," *J. Biol. Chem.* 275(24):18574-18580.

Stojadinovic, O. et al., 2005, Molecular Pathogenesis of Chronic Wounds: The Role of β-Catenin and c-myc in the Inhibition of Epithelialization and Wound Healing,: *Am J Pathol*, 167(1):59-69.

Suzuki, A. et al., 2000, "Meltrin α cytoplasmic domain interacts with SH3 domains of Src and Grb2 and is phosphorylated by v-Src," *Oncogene* 19:5842 5850.

Tomic-Canic, M., 2005, "Keratinocyte Cross-Talks in Wounds," *Wounds*, September Suppl:3-5.

Veves, A. et al., 2001, "Graftskin, a Human Skin Equivalent, is Effective in the Management of Noninfected Neuropathic Diabetic Foot Ulcers," *Diabetes Care* 24(2):290 295.

Wu, E. et al., 1997, "Expression of Members of the Novel Membrane Linked Metalloproteinase Family ADAM in Cells Derived from a Range of Haematological Malignancies,"*Biochem. Biophys. Res. Commun.* 235:437 442.

\* cited by examiner

LOCUS       NM_003474  5504 bp    mRNA    linear    PRI 18 NOV 2006
DEFINITION  Homo sapiens ADAM metallopeptidase domain 12(meltrin alpha)
            (ADAM12), transcript variant 1, mRNA.
ACCESSION   NM_003474
VERSION     NM_003474.3  GI:73747884
KEYWORDS
SOURCE Homo sapiens (human)

```
   1 GACTGCTGGC CGTGGATCCA TTTCACAGGC CTGCCTTCTC TCACTAACGC TCTTCCTAGT
  61 CCCCGGGCCA ACTCGGACAG TTTGCTCATT TATTGCAACG GTCAAGGCTG GCTTGTGCCA
 121 GAACGGCGCG CGCGCGCGCA CGCACGCACA CACACGGGGG GAAACTTTTT TAAAAATGAA
 181 AGGCTAGAAG AGCTCAGCGG CGGCGCGGGC GCTGCGCGAG GCTCCGGAG  CTGACTCGCC
 241 GAGGCAGGAA ATCCCTCCGG TCGCGACGCC CGGCCCCGGC TCGGCGCCCG CGTGGGATGG
 301 TGCAGCGCTC GCCGCCGGGC CCGAGAGCTG CTGCACTGAA GGCCGGCGAC GATGGCAGCG
 361 CGCCCGCTGC CCGTGTCCCC CGCCCGCGCC CTCCTGCTCG CCCTGGCCGG TGCTCTGCTC
 421 GCGCCCTGCG AGGCCCGAGG GGTGAGCTTA TGGAACCAAG GAAGAGCTGA TGAAGTTGTC
 481 AGTGCCTCTG TTGGGAGTGG GGACCTCTGG ATCCCAGTGA AGAGCTTCGA CTCCAAGAAT
 541 CATCCAGAAG TGCTGAATAT CGACTACAA  CGGGAAAGCA AGAACTGAT  CATAAATCTG
 601 GAAAGAAATG AAGGTCTCAT TGCCAGCAGT TTCACGGAAA CCCACTATCT GCAAGACGGT
 661 ACTGATGTCT CCCTCGCTCG AAATTACACG GTAATTCTGG GTCACTGTTA CTACCATGGA
 721 CATGTACGGG GATATTCTGA TTCAGCAGTC AGTCTCAGCA CGTGTTCTGG TCTCAGGGGA
 781 CTTATTGTGT TTGAAAATGA AAGCTATGTC TTAGAACCAA TGAAAAGTGC AACCAACAGA
 841 TACAAACTCT TCCCAGCGAA GAAGCTGAAA AGCGTCCGGG GATCATGTGG ATCACATCAC
 901 AACACACCAA ACCTCGCTGC AAAGAATGTG TTTCCACCAC CCTCTCAGAC ATGGGCAAGA
 961 AGGCATAAAA GAGAGACCCT CAAGGCAACT AAGTATGTGG AGCTGGTGAT CGTGGCAGAC
1021 AACCGAGAGT TCAGAGGCAA AGGAAAAGAT CTGGAAAAAG TTAAGCAGCG ATTAATAGAG
```

FIG. 2A

```
1081 ATTGCTAATC ACGTTGACAA GTTTTACAGA CCACTGAACA TTCGGATCGT GTTGGTAGGC

1141 GTGGAAGTGT GGAATGACAT GGACAAATGC TCTGTAAGTC AGGACCCATT CACCAGCCTC

1201 CATGAATTTC TGGACTGGAG GAAGATGAAG CTTCTACCTC GCAAATCCCA TGACAATGCG

1261 CAGCTTGTCA GTGGGGTTTA TTTCCAAGGG ACCACCATCG GCATGGCCCC AATCATGAGC

1321 ATGTGCACGG CAGACCAGTC TGGGGGAATT GTCATGGACC ATTCAGACAA TCCCCTTGGT

1381 GCAGCCGTGA CCCTGGCACA TGAGCTGGGC CACAATTTCG GGATGAATCA TGACACACTG

1441 GACAGGGGCT GTAGCTGTCA AATGGCGGTT GAGAAAGGAG CTGCATCAT GAACGCTTCC

1501 ACCGGGTACC CATTTCCCAT GGTGTTCAGC AGTTGCAGCA GGAAGGACTT GGAGACCAGC

1561 CTGGAGAAAG GAATGGGGGT GTGCCTGTTT AACCTGCCGG AAGTCAGGGA GTCTTTCGGG

1621 GGCCAGAAGT GTGGGAACAG ATTTGTGGAA GAAGGAGAGG AGTGTGACTG TGGGGAGCCA

1681 GAGGAATGTA TGAATCGCTG CTGCAATGCC ACCACCTGTA CCCTGAAGCC GGACGCTGTG

1741 TGCGCACATG GCTGTGCTG TGAAGACTGC CAGCTGAAGC CTGCAGGAAC AGCGTGCAGG

1801 GACTCCAGCA ACTCCTGTGA CCTCCCAGAG TTCTGCACAG GGGCCAGCCC TCACTGCCCA

1861 GCCAACGTGT ACCTGCACGA TGGGCACTCA TGTCAGGATG TGGACGGCTA CTGCTACAAT

1921 GGCATCTGCC AGACTCACGA GCAGCAGTGT GTCACGCTCT GGGGACCAGG TGCTAAACCT

1981 GCCCCTGGGA TCTGCTTTGA GAGAGTCAAT TCTGCAGGTG ATCCTTATGG CAACTGTGGC

2041 AAAGTCTCGA AGAGTTCCTT TGCCAAATGC GAGATGAGAG ATGCTAAATG TGGAAAAATC

2101 CAGTGTCAAG GAGGTGCCAG CCGGCCAGTC ATTGGTACCA ATGCCGTTTC CATAGAAACA

2161 AACATCCCCC TGCAGCAAGG AGGCCGGATT CTGTGCCGGG GACCCACGT GTACTTGGGC

2221 GATGACATGC CGGACCCAGG GCTTGTGCTT GCAGGCACAA AGTGTGCAGA TGGAAAAATC

2281 TGCCTGAATC GTCAATGTCA AAATATTAGT GTCTTTGGGG TTCACGAGTG TGCAATGCAG

2341 TGCCACGGCA GAGGGGTGTG CAACAACAGG AAGAACTGCC ACTGCGAGGC CCACTGGGCA

2401 CCTCCCTTCT GTGACAAGTT TGGCTTTGGA GGAAGCACAG ACAGCGGCCC CATCCGGCAA

2461 GCAGATAACC AAGGTTTAAC CATAGGAATT CTGGTGACCA TCCTGTGTCT TCTTGCTGCC

2521 GGATTTGTGG TTTATCTCAA AAGGAAGACC TTGATACGAC TGCTGTTTAC AAATAAGAAG
```

FIG. 2A

2581 ACCACCATTG AAAAACTAAG GTGTGTGCGC CCTTCCCGGC CACCCCGTGG CTTCCAACCC

2641 TGTCAGGCTC ACCTCGGCCA CCTTGGAAAA GGCCTGATGA GGAAGCCGCC AGATTCCTAC

2701 CCACCGAAGG ACAATCCCAG GAGATTGCTG CAGTGTCAGA ATGTTGACAT CAGCAGACCC

2761 CTCAACGGCC TGAATGTCCC TCAGCCCCAG TCAACTCAGC GAGTGCTTCC TCCCCTCCAC

2821 CGGGCCCCAC GTGCACCTAG CGTCCCTGCC AGACCCCTGC CAGCCAAGCC TGCACTTAGG

2881 CAGGCCCAGG GGACCTGTAA GCCAAACCCC CCTCAGAAGC CTCTGCCTGC AGATCCTCTG

2941 GCCAGAACAA CTCGGCTCAC TCATGCCTTG GCCAGGACCC CAGGACAATG GGAGACTGGG

3001 CTCCGCCTGG CACCCCTCAG ACCTGCTCCA CAATATCCAC ACCAAGTGCC CAGATCCACC

3061 CACACCGCCT ATATTAAGTG AGAAGCCGAC ACCTTTTTC AACAGTGAAG ACAGAAGTTT

3121 GCACTATCTT TCAGCTCCAG TTGGAGTTTT TTGTACCAAC TTTTAGGATT TTTTTTAATG

3181 TTTAAAACAT CATTACTATA GAACTTTGA GCTACTGCCG TCAGTGCTGT GCTGTGCTAT

3241 GGTGCTCTGT CTACTTGCTC AGGTACTTGT AAATTATTAA TTTATGCAGA ATGTTGATTA

3301 CAGTGCAGTG CGCTGTAGTA GGCATTTTTA CCATCACTGA GTTTTCCATG GCAGGAAGGC

3361 TTGTTGTGCT TTTAGTATTT TAGTGAACTT GAAATATCCT GCTTGATGGG ATTCTGGACA

3421 GGATGTGTTT GCTTTCTGAT CAAGGCCTTA TTGGAAAGCA GTCCCCCAAC TACCCCCAGC

3481 TGTGCTTATG GTACCAGATG CAGCTCAAGA GATCCCAAGT AGAATCTCAG TTGATTTTCT

3541 GGATTCCCCA TCTCAGGCCA GAGCCAAGGG GCTTCAGGTC CAGGCTGTGT TTGGCTTTCA

3601 GGGAGGCCCT GTGCCCCTTG ACAACTGGCA GGCAGGCTCC CAGGGACACC TGGGAGAAAT

3661 CTGGCTTCTG CCAGGAAGC TTTGGTGAGA ACCTGGGTTG CAGACAGGAA TCTTAAGGTG

3721 TAGCCACACC AGGATAGAGA CTGGAACACT AGACAAGCCA GAACTTGACC CTGAGCTGAC

3781 CAGCCGTGAG CATGTTTGGA AGGGGTCTGT AGTGTCACTC AAGGCGGTGC TTGATAGAAA

3841 TGCCAAGCAC TTCTTTTTCT CGCTGTCCTT TCTAGAGCAC TGCCACCAGT AGGTTATTTA

3901 GCTTGGGAAA GGTGGTGTTT CTGTAAGAAA CCTACTGCCC AGGCACTGCA AACCGCCACC

3961 TCCCTATACT GCTTGGAGCT GAGCAAATCA CCACAAACTG TAATACAATG ATCCTGTATT

4021 CAGACAGATG AGGCTTTCCA TGGGACCACA ACTATTTTCA GATGTGAACC ATTAACCAGA

FIG. 2A

```
4081 TCTAGTCAAT CAAGTCTGTT TACTGCAAGG TTCAACTTAT TAACAATTAG GCAGACTCTT

4141 TATGCTTGCA AAAACTACAA CCAATGGAAT GTGATGTTCA TGGGTATAGT TCATGTCTGC

4201 TATCATTATT CGTAGATATT GGACAAAGAA CCTTCTCTAT GGGGCATCCT CTTTTTCCAA

4261 CTTGGCTGCA GGAATCTTTA AAAGATGCTT TTAACAGAGT CTGAACCTAT TTCTTAAACA

4321 CTTGCAACCT ACCTGTTGAG CATCACAGAA TGTGATAAGG AAATCAACTT GCTTATCAAC

4381 TTCCTAAATA TTATGAGATG CTGGCTTGGG CAGCATCCCC TTGAACTCTT CACTCTTCAA

4441 ATGCCTGACT AGGGAGCCAT GTTTCACAAG GTCTTTAAAG TGACTAATGG CATGAGAAAT

4501 ACAAAAATAC TCAGATAAGG TAAAATGCCA TGATGCCTCT GTCTTCTGGA CTGGTTTTCA

4561 CATTAGAAGA CAATTGACAA CAGTTACATA ATTCACTCTG AGTGTTTTAT GAGAAAGCCT

4621 TCTTTTGGGG GTCAACAGTT TTCCTATGCT TTGAAACAGA AAAATATGTA CCAAGAATCT

4681 TGGTTTGCCT TCCAGAAAAC AAAACTGCAT TCACTTTCC CGGTGTTCCC CACTGTATCT

4741 AGGCAACATA GTATTCATGA CTATGGATAA ACTAAACACG TGACACAAAC ACACACAAAA

4801 GGGAACCCAG CTCTAATACA TTCCAACTCG TATAGCATGC ATCTGTTTAT TCTATAGTTA

4861 TTAAGTTCTT TAAAATGTAA AGCCATGCTG GAAAATAATA CTGCTGAGAT ACATACAGAA

4921 TTACTGTAAC TGATTACACT TGGTAATTGT ACTAAAGCCA ACATATATA TACTATTAAA

4981 AAGGTTTACA GAATTTTATG GTGCATTACG TGGGCATTGT CTTTTTAGAT GCCCAAATCC

5041 TTAGATCTGG CATGTTAGCC CTTCCTCCAA TTATAAGAGG ATATGAACTG AGTTTTTCTT

5101 TTGTTGTTTG TTCTTAGCTG TAATTCCTAT GCTTCTATTT CAGAGAGCCA GGAGAGTTTG

5161 ATATTAAAGG AGGTTAAAAC TGTGATCTTA TGCCATGTCA TCAATGGCCA CTTAGGGGCC

5221 ATGGCTGATG ACACATTCTT ATCTCTACAG TACTAATGTG TTATTATAGA GCCATGCATT

5281 TTATTTCTGA ATAAGAACAT ATTTAAACTA ATATTCCCTT ACAATATGGA CAGTATTAAT

5341 CCTTCCAAGA TGCAGTATTT ATCAAGTGAA GCATATTTAG CAGCAAATTC CATTTTAACA

5401 TAACTTAGGA ACCAATAACC AGGGTGTTTT GTGGTTGGGG GAGGCACGGG GTGGAGTATT

5461 CTTTTTTATA TCCTCAAAAC AAAAAAAATC AATACTTATA TTTC
```

FIG. 2A

```
  1  MAARPLPVSP ARALLLALAG ALLAPCEARG VSLWNQGRAD EVVSASVGSG DLWIPVKSFD
 61  SKNHPEVLNI RLQRESKELI INLERNEGLI ASSFTETHYL QDGTDVSLAR NYTVILGHCY
121  YHGHVRGYSD SAVSLSTCSG LRGLIVFENE SYVLEPMKSA TNRYKLFPAK KLKSVRGSCG
181  SHHNTPNLAA KNVFPPPSQT WARRHKRETL KATKYVELVI VADNREFQRQ GKDLEKVKQR
241  LIEIANHVDK FYRPLNIRIV LVGVEVWNDM DKCSVSQDPF TSLHEFLDWR KMKLLPRKSH
301  DNAQLVSGVY FQGTTIGMAP IMSMCTADQS GGIVMDHSDN PLGAAVTLAH ELGHNFGMNH
361  DTLDRGCSCQ MAVEKGGCIM NASTGYPFPM VFSSCSRKDL ETSLEKGMGV CLFNLPEVRE
421  SFGGQKCGNR FVEEGEECDC GEPEECMNRC CNATTCTLKP DAVCAHGLCC EDCQLKPAGT
481  ACRDSSNSCD LPEFCTGASP HCPANVYLHD GHSCQDVDGY CYNGICQTHE QQCVTLWGPG
541  AKPAPGICFE RVNSAGDPYG NCGKVSKSSF AKCEMRDAKC GKIQCQGGAS RPVIGTNAVS
601  IETNIPLQQG GRILCRGTHV YLGDDMPDPG LVLAGTKCAD GKICLNRQCQ NISVFGVHEC
661  AMQCHGRGVC NNRKNCHCEA HWAPPFCDKF GFGGSTDSGP IRQADNQGLT IGILVTILCL
721  CATGTACGGG GATATTCTGA TTCAGCAGTC AGTCTCAGCA CGTGTTCTGG TCTCAGGGGA
781  DSYPPKDNPR RLLQCQNVDI SRPLNGLNVP QPQSTQRVLP PLHRAPRAPS VPARPLPAKP
841  ALRQAQGTCK PNPPQKPLPA DPLARTTRLT HALARTPGQW ETGLRLAPLR PAPQYPHQVP
901  RSTHTAYIK 208-909 = mature ADAM12 isoform or variant 1 (ADAM12-L)

204-413 = metalloprotease domain 414-509 = disintegrin domain 510-704 = cysteine-rich domain 705-725 = transmembrane domain 726-906 = cytoplasmic tail
```

FIG. 2B

```
LOCUS       NM_021641  3355 bp    mRNA     linear   PRI 18 NOV 2006
DEFINITION  Homo sapiens ADAM metallopeptidase domain 12 (meltrin alpha)
            (ADAM12), transcript variant 2, mRNA.
ACCESSION   NM_021641
VERSION NM_021641.2  GI:73747886
KEYWORDS
SOURCE Homo sapiens (human)
    1 GACTGCTGGC CGTGGATCCA TTTCACAGGC CTGCCTTCTC TCACTAACGC TCTTCCTAGT
   61 CCCCGGGCCA ACTCGGACAG TTTGCTCATT TATTGCAACG GTCAAGGCTG GCTTGTGCCA
  121 GAACGGCGCG CGCGCGCGCA CGCACGCACA CACACGGGGG GAAACTTTTT TAAAAATGAA
  181 AGGCTAGAAG AGCTCAGCGG CGGCGCGGGC GCTGCGCGAG GGCTCCGGAG CTGACTCGCC
  241 GAGGCAGGAA ATCCCTCCGG TCGCGACGCC CGGCCCCGGC TCGGCGCCCG CGTGGGATGG
  301 TGCAGCGCTC GCCGCCGGGC CCGAGAGCTG CTGCACTGAA GGCCGGCGAC GATGGCAGCG
  361 CGCCCGCTGC CCGTGTCCCC CGCCCGCGCC CTCCTGCTCG CCCTGGCCGG TGCTCTGCTC
  421 GCGCCCTGCG AGGCCCGAGG GGTGAGCTTA TGGAACCAAG GAAGAGCTGA TGAAGTTGTC
  481 AGTGCCTCTG TTGGGAGTGG GGACCTCTGG ATCCCAGTGA AGAGCTTCGA CTCCAAGAAT
  541 CATCCAGAAG TGCTGAATAT TCGACTACAA CGGGAAAGCA AGAACTGAT CATAAATCTG
  601 GAAAGAAATG AAGGTCTCAT TGCCAGCAGT TTCACGGAAA CCCACTATCT GCAAGACGGT
  661 ACTGATGTCT CCCTCGCTCG AAATTACACG GTAATTCTGG GTCACTGTTA CTACCATGGA
  721 CATGTACGGG GATATTCTGA TTCAGCAGTC AGTCTCAGCA CGTGTTCTGG TCTCAGGGGA
  781 CTTATTGTGT TTGAAAATGA AAGCTATGTC TTAGAACCAA TGAAAAGTGC AACCAACAGA
  841 TACAAACTCT CCCAGCGAA GAAGCTGAAA AGCGTCCGGG GATCATGTGG ATCACATCAC
  901 AACACACCAA ACCTCGCTGC AAAGAATGTG TTTCCACCAC CCTCTCAGAC ATGGGCAAGA
  961 AGGCATAAAA GAGAGACCCT CAAGGCAACT AAGTATGTGG AGCTGGTGAT CGTGGCAGAC
 1021 AACCGAGAGT TCAGAGGCA AGGAAAAGAT CTGGAAAAAG TTAAGCAGCG ATTAATAGAG
```

FIG. 3A

```
1081 ATTGCTAATC ACGTTGACAA GTTTTACAGA CCACTGAACA TTCGGATCGT GTTGGTAGGC
1141 GTGGAAGTGT GGAATGACAT GGACAAATGC TCTGTAAGTC AGGACCCATT CACCAGCCTC
1201 CATGAATTTC TGGACTGGAG GAAGATGAAG CTTCTACCTC GCAAATCCCA TGACAATGCG
1261 CAGCTTGTCA GTGGGGTTTA TTTCCAAGGG ACCACCATCG GCATGGCCCC AATCATGAGC
1321 ATGTGCACGG CAGACCAGTC TGGGGGAATT GTCATGGACC ATTCAGACAA TCCCCTTGGT
1381 GCAGCCGTGA CCCTGGCACA TGAGCTGGGC CACAATTTCG GATGAATCA TGACACACTG
1441 GACAGGGGCT GTAGCTGTCA AATGGCGGTT GAGAAAGGAG GCTGCATCAT GAACGCTTCC
1501 ACCGGGTACC CATTTCCCAT GGTGTTCAGC AGTTGCAGCA GGAAGGACTT GGAGACCAGC
1561 CTGGAGAAAG GAATGGGGGT GTGCCTGTTT AACCTGCCGG AAGTCAGGGA GTCTTTCGGG
1621 GGCCAGAAGT GTGGGAACAG ATTTGTGGAA GAAGGAGAGG AGTGTGACTG TGGGGAGCCA
1681 GAGGAATGTA TGAATCGCTG CTGCAATGCC ACCACCTGTA CCCTGAAGCC GGACGCTGTG
1741 TGCGCACATG GGCTGTGCTG TGAAGACTGC CAGCTGAAGC CTGCAGGAAC AGCGTGCAGG
1801 GACTCCAGCA ACTCCTGTGA CCTCCCAGAG TTCTGCACAG GGGCCAGCCC TCACTGCCCA
1861 GCCAACGTGT ACCTGCACGA TGGGCACTCA TGTCAGGATG TGGACGGCTA CTGCTACAAT
1921 GGCATCTGCC AGACTCACGA GCAGCAGTGT GTCACGCTCT GGGGACCAGG TGCTAAACCT
1981 GCCCCTGGGA TCTGCTTTGA GAGAGTCAAT TCTGCAGGTG ATCCTTATGG CAACTGTGGC
2041 AAAGTCTCGA AGAGTTCCTT TGCCAAATGC GAGATGAGAG ATGCTAAATG TGGAAAAATC
2101 CAGTGTCAAG GAGGTGCCAG CCGGCCAGTC ATTGGTACCA ATGCCGTTTC CATAGAAACA
2161 AACATCCCCC TGCAGCAAGG AGGCCGGATT CTGTGCCGGG GACCCACGT GTACTTGGGC
2221 GATGACATGC CGGACCCAGG GCTTGTGCTT GCAGGCACAA AGTGTGCAGA TGGAAAAATC
2281 TGCCTGAATC GTCAATGTCA AAATATTAGT GTCTTTGGGG TTCACGAGTG TGCAATGCAG
2341 TGCCACGGCA GAGGGGTGTG CAACAACAGG AAGAACTGCC ACTGCGAGGC CCACTGGGCA
2401 CCTCCCTTCT GTGACAAGTT TGGCTTTGGA GGAAGCACAG ACAGCGGCCC CATCCGGCAA
2461 GCAGAAGCAA GGCAGGAAGC TGCAGAGTCC AACAGGGAGC GCGGCCAGGG CCAGGAGCCC
2521 GTGGGATCGC AGGAGCATGC GTCTACTGCC TCACTGACAC TCATCTGAGC CCTCCCATGA
```

FIG. 3A

```
2581  CATGGAGACC GTGACCAGTG CTGCTGCAGA GGAGGTCACG CGTCCCCAAG GCCTCCTGTG

2641  ACTGGCAGCA TTGACTCTGT GGCTTTGCCA TCGTTTCCAT GACAACAGAC ACAACACAGT

2701  TCTCGGGGCT CAGGAGGGGA AGTCCAGCCT ACCAGGCACG TCTGCAGAAA CAGTGCAAGG

2761  AAGGGCAGCG ACTTCCTGGT TGAGCTTCTG CTAAAACATG GACATGCTTC AGTGCTGCTC

2821  CTGAGAGAGT AGCAGGTTAC CACTCTGGCA GGCCCCAGCC CTGCAGCAAG GAGGAAGAGG

2881  ACTCAAAAGT CTGGCCTTTC ACTGAGCCTC CACAGCAGTG GGGGAGAAGC AAGGGTTGGG

2941  CCCAGTGTCC CCTTTCCCCA GTGACACCTC AGCCTTGGCA GCCCTGATGA CTGGTCTCTG

3001  GCTGCAACTT AATGCTCTGA TATGGCTTTT AGCATTTATT ATATGAAAAT AGCAGGGTTT

3061  TAGTTTTTAA TTTATCAGAG ACCCTGCCAC CCATTCCATC TCCATCCAAG CAAACTGAAT

3121  GGCAATGAAA CAAACTGGAG AAGAAGGTAG GAGAAAGGGC GGTGAACTCT GGCTCTTTGC

3181  TGTGGACATG CGTGACCAGC AGTACTCAGG TTTGAGGGTT TGCAGAAAGC CAGGGAACCC

3241  ACAGAGTCAC CAACCCTTCA TTTAACAAGT AAGAATGTTA AAAAGTGAAA ACAATGTAAG

3301  AGCCTAACTC CATCCCCCGT GGCCATTACT GCATAAAATA GAGTGCATTT GAAAT
```

FIG. 3A

▼
1   MAARPLPVSP ARALLLALAG ALLAPCEARG VSLWNQGRAD EVVSASVGSG DLWIPVKSFD

61  SKNHPEVLNI RLQRESKELI INLERNEGLI ASSFTETHYL QDGTDVSLAR NYTVILGHCY

121 YHGHVRGYSD SAVSLSTCSG LRGLIVFENE SYVLEPMKSA TNRYKLFPAK KLKSVRGSCG

181 SHHNTPNLAA KNVFPPPSQT WARRHKRETL KATKYVELVI VADNREFQRQ GKDLEKVKQR

241 LIEIANHVDK FYRPLNIRIV LVGVEVWNDM DKCSVSQDPF TSLHEFLDWR KMKLLPRKSH

301 DNAQLVSGVY FQGTTIGMAP IMSMCTADQS GGIVMDHSDN PLGAAVTLAH ELGHNFGMNH

361 DTLDRGCSCQ MAVEKGGCIM NASTGYPFPM VFSSCSRKDL ETSLEKGMGV CLFNLPEVRE

421 SFGGQKCGNR FVEEGEECDC GEPEECMNRC CNATTCTLKP DAVCAHGLCC EDCQLKPAGT

481 ACRDSSNSCD LPEFCTGASP HCPANVYLHD GHSCQDVDGY CYNGICQTHE QQCVTLWGPG

541 AKPAPGICFE RVNSAGDPYG NCGKVSKSSF AKCEMRDAKC GKIQCQGGAS RPVIGTNAVS

601 IETNIPLQQG GRILCRGTHV YLGDDMPDPG LVLAGTKCAD GKICLNRQCQ NISVFGVHEC

661 AMQCHGRGVC NNRKNCHCEA HWAPPFCDKF GFGGSTDSGP IRQAEARQEA AESNRERGQG

721 QEPVGSQEHA STASLTLI 208-738 = mature ADAM12 isoform or variant 2 (ADAM12-S)

207-416 = metalloprotease domain 417-512 = disintegrin domain 513-701 = cysteine-rich domain

FIG. 3B

METHODS AND COMPOSITIONS FOR PROMOTING WOUND HEALING

CROSS REFERENCE TO RELATED APPLICATIONS

This application claims benefit under 35 U.S.C. §119(e) to application Ser. No. 60/918,367, filed Mar. 15, 2007, the contents of which is incorporated herein by reference.

STATEMENT REGARDING FEDERALLY SPONSORED RESEARCH

The United States Government may have certain rights in this invention pursuant to Grant No. GM64750 and NR008029 awarded by the National Institutes of Health.

BACKGROUND

Chronic wounds represent a major health burden worldwide, and a significant drain on medical resources. For example, recent studies have calculated the annual cost of chronic wounds to the NHS in the United Kingdom to be approximately £1 billion (Harding, "The Future of Wound Healing," In: Leaper et al., *Wounds: Biology and Management*," Oxford University Press, 1998 at page 191). Foot ulceration, the most common complication of diabetes requiring hospitalization, is estimated to cost the UK approximately £17 million per year (Currie et al., 1998, *Diabetes Care* 21:42-48) and the US approximately $150 million per year (Reiber et al., 1992, *Diabetes Care* 15(suppl. 1):29-31). The total annual cost of diabetic peripheral neuropathy and its complications in the US was estimated to be between $4.6 and $13.7 billion (Gordois, et al., 2003, *Diabetes Care* 26:1790-1795). Equally, or even more costly are managing and treating pressure ulcers (bed sores)—$55 billion annually—and venous leg ulcers—estimated to be 2.5 to 3 billion US dollars, with a loss of 2 million work days per year (McGuckin, et al., 2001, *Adv Skin Wound Care* 14(1):33-36; and see decubitus.org/cost/cost.html).

These sums show only the economic costs of managing and treating chronic wounds. They do not reflect the frustration, economic loss and impaired quality of life experienced by patients with chronic wounds. Indeed, deep foot ulcers may be accompanied by cellulites or osteomyelitis, and a severely infected or nonhealing foot ulcer may require amputation of the toe, foot or leg (Gordois, et al., 2003, *Diabetes Care* 26:1790-1795).

Recent understandings of the biology underlying wound healing have led to the development of several new and experimental treatments. These include: the use of dressings designed to promote wound healing; topical administration of growth factors such as transforming growth factor beta, which is currently being studied for use in venous ulcers, platelet derived growth factor, which has been licensed for the treatment of diabetic foot ulcers (becaplermin, Regranex) and has shown some promise in treating pressure ulcers (Rees, 1997, *Wound Repair Regen.* 7:141-147), granulocyte colony stimulating factor, which has been evaluated for the treatment of infected diabetic foot ulcers (Gough, 1997, *Lancet* 350: 833-859), fibroblast growth factor, which has been assessed for treating pressure ulcers (Robson et al., 1992, *Ann. Surg.* 216(40):401-408), and epidermal growth factor, which has been used to treat venous leg ulcers (Falanga et al., 1992, *J. Dermatol. Surg. Oncol.* 18:604-606); autologous skin grafts, which have been successfully used to treat venous leg ulcers (Mauro, T. M., 1992, *West J. Med.* 156(2): 191); and bioengineered skin equivalents such as Alloderm (a dermal matrix without immunogenic cells), Integra (a combination of dermal fibroblasts and bovine collagen), Dermagraft (non-immunogenic neonatal fibroblasts cultured in a polyglactin mesh) and Apilgraf (contains both epidermal and dermal components). All of these bioengineered skin grafts have been used to treat burns. Dermagraft has also been used to treat diabetic foot ulcers (Gentzkow et al., 1996, *Diabetes Care* 19:350-354). Apilgraf has been used to treat diabetic foot ulcers (Veves et al., 2001, *Diabetes Care* 24:290-295) and venous leg ulcers (Falanga et al., 1998, *Arch. Dermatol.* 134:293-300).

Unfortunately, clinical results with these new technologies have not been as dramatic as hoped. Accordingly, there remains a need in the art for new strategies and compositions for the treatment of wounds generally, and chronic wounds specifically.

SUMMARY

ADAM12 (A disintegrin and metalloprotease 12) is a membrane anchored metalloprotease that has been implicated in the cleavage of insulin-like growth factor-binding protein-3 in blood during pregnancy (Shi et al., 2000, *J. Biol. Chem.* 275:18574-18580) and in the progression of several diseases, including human tumorgenic cancer (Iba et al., 1999, *Am. J. Pathol.* 154:1489-1501), prostate cancer (Peduto et al., 2006, *Oncogene,* 25:5462-5466), hematological malignancies (Wu et al., 1997, *Biochem. Biophys. Res. Commun.* 235:437-442) and cardiac hypertrophy (Asakura et al., 2002, *Nat. Med.* 8:35-40). As will be discussed in more detail below, compelling evidence reported herein suggests that in addition to these biological functions, ADAM12 is an important mediator of wound healing and pathogenesis. For example, it has been discovered that ADAM12 is up-regulated in chronic wounds. Specifically, it has been discovered that the amount of ADAM12 expressed in the non-healing edge of chronic skin ulcers is approximately at least five-fold greater than that observed in normal skin. In addition, studies with skin explants from ADAM12 knock-out mice revealed a statistically significant increase in the migration of keratinocytes as compared to skin explants from wild-type mice in samples that were either treated or untreated with EGF. While not intending to be bound by any theory of operation, these studies suggest that increased expression of ADAM12 in chronic wounds impairs wound healing through the inhibition of keratinocyte migration, and that compounds capable of inhibiting the activity or expression of ADAM12 would provide a new and powerful means of promoting healing of wounds.

Accordingly, in one aspect, the present disclosure provides methods of inhibiting ADAM12 activity or expression as a therapeutic approach towards the treatment and/or promotion of healing of wounds. In some embodiments, the methods comprise administering to a wound an amount of an ADAM12 inhibitory compound effective to treat and/or promote healing of the wound. The ADAM12 inhibitory compound can inhibit an activity of an ADAM12 polypeptide per se or expression of one or more Adam12 gene products. As specific examples, ADAM12 inhibitory compounds that inhibit expression of an Adam12 gene product can inhibit transcription of a gene encoding an ADAM12, thereby blocking synthesis of ADAM12 mRNA, or translation of mRNA encoding an ADAM12, thereby blocking synthesis of ADAM12 polypeptides. Compounds useful for inhibiting an activity of an ADAM12 polypeptide per se include, by way of example and not limitation, small molecules, antibodies, polypeptides, polynucleotides, or other ADAM12 antagonists. Compounds useful for inhibiting expression of Adam12 gene products include, by way of example and not limitation, antisense, siRNA and miRNA oligonucleotides.

The ADAM12 inhibitory compounds can be administered by any means suitable for the delivery of the specific ADAM12 inhibitory compound being utilized. The treatment can be applied systemically, or alternatively, the ADAM12 inhibitory compound can be applied locally directly to the wound, for example by way of injection directly into the wounded tissue or by way of a topical formulation containing the ADAM12 inhibitory compound. Non-limiting examples of suitable local or topical formulations include sprays, liquids, gels, creams, ointments, transdermal patches and wound dressings. Embodiments in which the wound being treated is an acute surgical wound, or a wound requiring suturing, the ADAM12 inhibitory compound can be administered with surgical sutures or staples that include, or that are coated with, the ADAM12 inhibitory compound.

The ADAM12 inhibitory compound may be administered alone, in combination with one or more additional ADAM12 inhibitory compounds and/or in combination with one or more additional therapeutic agents. Some examples of such therapeutic agents that can be used in combination therapies include, but are not limited to, Regranex, becaplermin, granulocyte colony stimulating factor, fibroblast growth factor, epidermal growth factor, agents that promote angiogenesis, and antibiotics.

In embodiments in which the ADAM12 inhibitory compound is a biological molecule, such as, for example, a peptide, polypeptide, oligonucleotide or polynucleotide, the inhibitory compound per se can be administered to the wound or patient, or alternatively, nucleic acids encoding the ADAM12 inhibitory compound can be administered to the wound or patient. In this latter embodiment, the cellular machinery of the body or wounded tissue is used as a means to express in vivo the ADAM12 inhibitory compound.

It is expected that virtually any type of wound can be treated with ADAM12 inhibitory compound(s) as described herein to promote healing. Of particular significance are wounds occurring in tissues that over-express ADAM12 as compared to unwounded tissue of the same type. Such over expression has been observed in human skin tissue of chronic wounds such as diabetic foot ulcers, venous leg ulcers and pressure ulcers, and is expected to be observed in other tissue types, including but not limited to mouth ulcers, gingiva, and corneal epithelium. Accordingly, it is expected that inhibition of ADAM12 activity and/or expression of one or more Adam12 gene products as described herein will be useful to treat a broad range of wounds, including both acute wounds such as injury and surgical wounds and chronic wounds such as diabetic foot ulcers, venous leg ulcers, arterial ulcers, pressure ulcers, mouth ulcers, gingival wounds and corneal wounds.

Furthermore, the usefulness of inhibiting ADAM12 activity and/or expression of one or more Adam12 gene products is not limited to the treatment of chronic wounds or tissues overexpressing ADAM12. In some tissues, ADAM12 expression levels may not be observed, and yet inhibitors may be useful to reduce ADAM12 expression to promote epithelialization. For example, inhibition of ADAM12 activity and/or expression of one or more Adam12 gene products as described herein is expected to be useful in treating acute wounds, surgical incisions, sickle cell ulcers, and corticosteroid-induced wounds.

In another aspect, the present disclosure provides compositions useful for administering ADAM12 inhibitory compounds to treat and/or promote healing of wounds as described herein. The compositions generally comprise one or more ADAM12 inhibitory compounds and can be formulated for systemic or local administration. Specific examples of compositions formulated for systemic administration include, by way of example and not limitation, oral, epidermal, transdermal, transmucosal (including vaginally and rectally), pulmonary (including inhalation or insufflation of powders or aerosols, or by nebulizer), intratracheal, intranasal, ophthalmic, intravenous, intraarterial, subcutaneous, intraperitoneal or intramuscular injection or infusion; or intracranial, e.g., intrathecal or intraventricular formulations. Specific examples of compositions suitable for local administration include, by way of example and not limitation, transdermal patches, skin coverings, wound dressings, sprays, foams, emulsions, liquids, powders, ointments, creams, lotions, gels, jellies, pastes, salves, tinctures, drops, liposome-containing formulations, suppositories, enemas, coated condoms and gloves.

In some embodiments, the composition is a wound dressing or packing designed to deliver the ADAM12 inhibitory compound directly to the wounded tissue.

BRIEF DESCRIPTION OF THE FIGURES

FIG. 2 provides the nucleotide sequence (SEQ ID NO: 1) of mRNA encoding the membrane anchored form of ADAM12 (splice variant 1; also called "ADAM12-L") (FIG. 2A), as well as the amino acid sequence (SEQ ID NO: 2) of the encoded ADAM12-L polypeptide (FIG. 2B);

FIG. 3 provides the nucleotide sequence (SEQ ID NO: 3) of mRNA encoding the secreted, short form of ADAM12 (splice variant 2; also called "ADAM12-S") (FIG. 3A), as well as the amino acid sequence (SEQ ID NO: 4) of the encoded ADAM12-S polypeptide (FIG. 3B);

DETAILED DESCRIPTION

Figure 1:
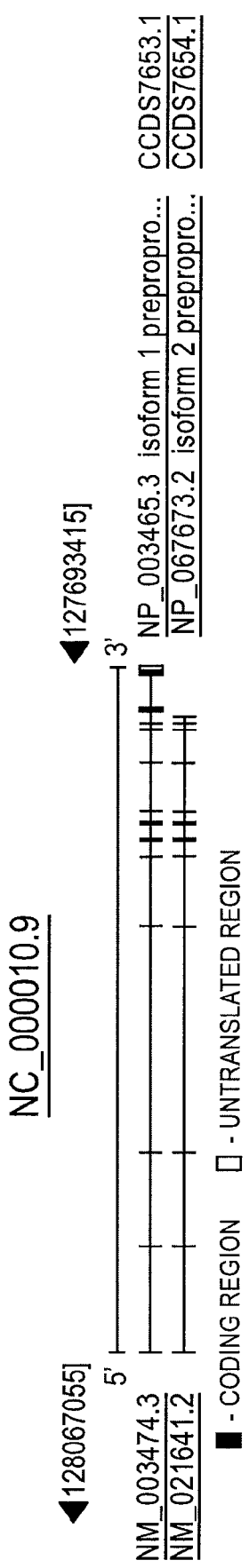
FIG. 1 is a graphic illustration of the human gene encoding ADAM12 (GENBANK Accession No. NC_000010.9) and its two mRNA variants.

The various inventions described herein are based upon the surprising discovery that one member of the family of metalloprotease disintegrins referred to as ADAMs, a disintegrin and metalloprotease 12 ("ADAM12"), is an important mediator of wound healing and pathogenesis.

The ADAMs are a family of almost 30 known multidomain proteins so named because they contain a disintegrin and metalloprotease domain. ADAMs share high sequence homology and domain organization with snake venom metalloproteases; both contain a metalloprotease-like domain with an associated regulatory prodomain, a disintegrin-like domain, a cysteine-rich domain, and an epidermal growth factor-like domain. In addition, ADAMs contain a transmembrane domain and a cytoplasmic tail (Evans, 2001, *BioEssays*

23:628-639). The metalloprotease domains are involved in cleavage of the amyloid precursor protein and ectodomain shedding of several membrane-anchored proteins, including tumor necrosis factors. The disintegrin and cysteine-rich domains play important roles in cell-cell and cell-matrix adhesion, cell differentiation, and fusion (Primakoff & Myles, 2000, *Trends Genet.* 16:83-87). The cytoplasmic tails contain consensus SH3-binding motifs, and have been shown to bind p85, Src, and alpha-actinin-1 and -2, suggesting that the cytoplasmic tail region is involved in signal transduction (Blobel, C. P., 1997, *Cell,* 90:589-592; Blobel, C. P., 2005, *Nat Rev Mol Cell Biol.* 6(1):32-43; Cao et al., 2001, *Biochem. J.* 357:353-361; Galliano et al., 2000, *J. Biol. Chem.* 275: 13933-13939; Kang et al., 2001, *J. Biol. Chem.* 276:24466-24472; Kang et al., 2000, *Biochem. J.* 352:883-892; Suzuki et al., 2000, *Oncogene,* 19:5842-5850).

ADAM12 was first identified in mice because of its involvement in myotube formation. During myoblast differentiation, the cells adhere to each other before their plasma membranes merge forming myotubes. The process of differentiation leading to cell fusion occurs in different tissues including placenta, bone, and muscle. ADAM12 was identified as a myoblast-expressed gene product and showed strong expression in neonatal skeletal muscle and bone (Yagami-Hiromasa et al., 1995, *Nature* 377:652-656).

The human gene encoding ADAM12 (also called meltrin-alpha) was cloned in 1998 and two isoforms were identified which arise from alternative splicing of a single gene (Gilpin et al., 1998, *J. Biol. Chem.* 273:157-166). The larger isoform is membrane-bound (designated ADAM12-L) and the shorter isoform (designated ADAM12-S) is secreted. The mRNA of both isoforms is abundant in human placenta and in some tumor cell lines. ADAM12-S has been identified as a possible protease responsible for the cleavage of insulin-like growth factor-binding protein-3 in blood during pregnancy (Shi et al., 2000, *J. Biol. Chem.* 275:18574-18580). The ADAM12-L transcript is also detected in human adult skeletal, cardiac, and smooth muscle. Human ADAM12 is an active metalloprotease and is synthesized as a zymogen, with the prodomain maintaining the metalloprotease in an a latent form (Loechel et al., 1998, *J. Biol. Chem.* 273:16993-16997; Loechel et al., 1999, *J. Biol. Chem.* 274:13427-13433).

The expression pattern of the ADAM12 transcripts examined during mouse embryogenesis revealed that the most prominent expression of ADAM12 is found in regions of bone formation. The ADAM12 gene is not activated in myotomes until myotube formation starts (Kurisaki et al., 1998, *Mech. Dev.* 73:211-215). The expression patterns of ADAM12 suggest that it is involved in cell fusion, but expression of ADAM12 is not restricted to fusagenic cells, suggesting a more general role for ADAM12. ADAM12 is also constitutively expressed in mouse C2 skeletal muscle cell fibroblasts (Kadota et al., 2000, *J. Biochem.* (Tokyo) 128:941-949), and ADAM12 mRNA has been detected in osteoblasts (Harris et al., 1997, *J. Cell. Biochem.* 67:136-142).

ADAM12, with its capacity to mediate cell adhesion, has been implicated in the progression of several diseases. ADAM12 expression is up-regulated in human carcinoma tissue and may have a role in human cancer by supporting tumor cell adhesion through the cysteine rich domain of ADAM12 (Iba et al., 1999, *Am. J. Pathol.* 154:1489-1501). ADAM12 has been reported to play a role in breast tumor progression and stromal cell apoptosis (Kveiborg et al., 2005, *Cancer Res.,* 65(11):4754-4761). Nude mice tumors generated from human rhabdomyosarcoma cells transfected with ADAM12-S contain a pattern of ectopic muscle cell formation as compared with control tumors. These tumors are of murine origin rather than derived from the human tumor cells, providing evidence that ADAM12-S provokes myogenesis in a nude mouse tumor model (Gilpin et al., 1998, *J. Biol. Chem.* 273:157-166).

The ADAM family of proteins may also be involved in the pathology associated with haematological malignancies. The cells derived from leukemia (HL60 and Jurkat), erythroleukemia (K562), lymphoma (U937 and Cupillo), and myeloma (U266B1) express mRNA of four members of the ADAM family, including ADAM12. It has been suggested that the metalloproteinase domains may be involved in egression of leukemic cells from the bone marrow into the peripheral blood, and that the integrin-like domain may be involved in adhesion-mediated migration mechanisms, such as that seen between bone marrow fibroblasts and erythroleukemia cell lines (Wu et al., 1997, *Biochem. Biophys. Res. Commun.* 235:437-442).

Cardiac hypertrophy is an adaptive response of the heart that occurs in various cardiovascular diseases, but prolonged hypertrophy typically culminates in chronic heart failure or sudden cardiac death. Inhibitors of metalloproteinases, in particular inhibitors of ADAM12, have been suggested as a therapeutic approach for cardiac hypertrophy. In cultured rat cardiomyocytes and in vivo, ADAM12 has been reported to cleave the membrane-anchored heparin-binding epidermal growth factor (HB-EGF) so that HB-EGF can induce a signaling cascade via G-protein coupled receptors leading to cardiac hypertrophy (Asakura et al., 2002, *Nat. Med.* 8:35-40).

Wound healing involves a complex interaction between epidermal and dermal cells, the extracellular matrix, controlled angiogenesis, and plasma derived proteins, all coordinated by an array of cytokines and growth factors. This dynamic process has been classically divided into several overlapping phases: inflammation, proliferation, migration and remodeling.

These various phases have been extensively studied and reviewed elsewhere. (See Martin, et al., 1997, *Science,* 276 (5309):75-81). Germane to the instant disclosure are the proliferation and migration stages. The combination of new tissue and contraction of surrounding tissues is essential for the healing of chronic skin ulcers (Clark, 1993, *Dermatol. Clin.* 11:657-666). Fibroblasts are the key cells involved in the production of new extracellular matrix (in addition to producing collagen they produce tenascin, fibronectin, and proteoglycans such as hyaluronic acid). While this new matrix is synthesized, existing matrix in and around the wound region is degraded by several enzyme systems, including matrix metalloproteinases and plasminogen activators. The effect of metalloproteinases is regulated by tissue inhibitors, which are believed to be important in healing by preventing excessive matrix degradation (March et al., 1994, *Arch. Dermatol. Res.* 287:107-114). At an injury site, keratinocytes are also a part of the primary response to injury, releasing a signal and mobilizing other cell types (macrophages, platelets, endothelial cells and fibroblasts) to the site of injury. In addition, keratinocytes respond to cellular signals by undergoing two processes: migration and proliferation. Both of these processes are important for complete epithelialization and wound closure. During healing, some keratinocytes at the wound edge proliferate. Others undergo a marked transformation to enable them to phagocytose debris and migrate across the wound bed. Keratinocyte migration, coupled with wound contraction, results in re-epithelialization and wound closure. However, the epidermal morphology of chronic wounds differs from the morphology of normal epidermis and suggests that keratinocytes do not successfully complete activation or differentiation in chronic wounds (Stojadinovic, et al., 2005, *Am J Pathol,* 167:59-69; Tomic-Canic, *Wounds,* Suppl:3-5; Morasso, et al., 2005, *Biol Cell,* 97:173-183; Brem, et al., 2007, *Molecular Medicine,* in press). Instead, keratinocytes are caught in a 'loop' of trying, but not succeeding, to accomplish either of the two processes. Keratinocytes at the non-healing edge of chronic wounds appear to be hyperproliferative but non-migratory, suggesting that lack of migration leads to inability to epithelialize and plays important role in pathogenesis of chronic ulcers.

Although ADAM12 has been implicated in tissue remodeling and activation/inactivation of various growth factors implicated in wound healing, such as the membrane-anchored heparin-binding epidermal growth factor (HB-EGF) and insulin-like growth factor (IGF) binding proteins, it has not been recognized as a key target or mediator of wound healing.

Compelling evidence reported herein suggests that ADAM12 plays a significant role in wound healing, and that inhibition of ADAM12 activity and/or expression represents a powerful new mechanism-based approach towards the treatment of chronic wounds, and may accelerate wound healing in general. For example, as reported in Example 1, microarray analyses carried out with the non-healing edge of chronic human skin ulcers revealed a five-fold increase in ADAM12 expression as compared to normal skin tissue. The results of these microarray analyses were confirmed in immunohistochemical assays using an antibody specific for ADAM12 (Example 2). A pronounced (between 5- and 6-fold) increase in signal from both membrane-bound and cytoplasmic ADAM12 was found in the epidermis of chronic wounds as compared to normal skin controls. These studies confirm that ADAM12 is upregulated in chronic skin ulcers as compared to normal skin.

ADAM12 also inhibits migration of keratinocytes, an important step in the proliferation phase of wound healing. As reported in Example 3, skin explants taken at birth from ADAM12 knock-out (ADAM12−/−) and wild-type (WT) mice placed in tissue culture for a period of seven days both in the presence and absence of epidermal growth factor (EGF) showed statistically significant differences in keratinocytes migration. Statistically significant increases in migration of ADAM12−/− keratinocytes as compared to WT keratinocytes were observed in both untreated (p=0.0001) and EGF-treated (p=0.028) samples.

These studies provide compelling evidence that ADAM12 is an important mediator of wound healing, and that inhibition of ADAM12 activity or expression provides a new, powerful therapeutic approach towards promoting healing of wounds in general, and in particular healing of chronic skin ulcers. The compositions and methods described herein take advantage of this surprising and new-found role of ADAM12.

While not intending to be bound by any theory of operation, it is hypothesized that the increased expression of ADAM12 in wound tissue reported herein impairs healing of the wound through inhibition of keratinocyte migration, an important step in the proliferation cycle of wound healing. Inhibition of ADAM12 activity and/or expression is expected to modulate this important step in the wound healing process, promoting healing of wounds.

Although the observations reported herein were observed in skin tissue from non-healing chronic wounds, it is expected that ADAM12 also plays an important role in mediating the healing of wound in other tissue types, such as, for example mouth tissue, gingiva, and corneal epithelium, and in tissues of non-chronic wounds. Accordingly, the ADAM12 inhibitory compounds described herein are expected to be useful for promoting healing of virtually any type of wound, including but not limited to, chronic skin ulcers such as diabetic foot ulcers, arterial ulcers, venous leg ulcers, and pressure ulcers (bed sores), mouth ulcers, sickle cell ulcers, and corticosteroid-induced wounds and acute wounds of the skin, caused from insults like injury and/or surgery.

In some embodiments, the ADAM12 inhibitory compounds described herein are used to treat and/or promote healing of wounded tissues that over-express an Adam12 gene product. As used herein, wound tissue "over-expresses an Adam12 gene product" if the wound tissue contains at least about 2-fold, and in some embodiments at least about 3-fold, 4-fold, 5-fold, or even higher, levels of an Adam12 gene product, such as, for example, mRNA encoding an ADAM12 polypeptide, and/or an ADAM12 polypeptide per se, as compared to unwounded tissue of the same type.

In some embodiments, the ADAM12 inhibitory compounds described herein are used to treat or promote healing of wounded tissues that do not over-express an Adam12 gene product.

As mentioned above, human ADAM12 is expressed in two forms arising from two different splicings of a single gene: a larger, membrane-bound form (designated herein as "ADAM12-L") and a shorter, secreted form (designated herein as "ADAM12-S") (Gilpin et al., 1998, *J. Biol. Chem.* 273:157-166). As used herein, the expression "ADAM12" is intended to encompass the ADAM12-L and/or ADAM12-S forms of the ADAM12 polypeptide. Thus, the expression "ADAM12" or "ADAM12 polypeptide" includes either or both the ADAM12-L and ADAM12-S forms of the polypeptide expressed by the Adam12 gene, and the expression "Adam12 gene product" includes mRNA encoding ADAM12-L, mRNA encoding ADAM12-S, or mRNA encoding both ADAM12-L and ADAM12-S.

In some embodiments, wound tissue that over-expresses an Adam12 gene product contains at least about 2-, 3-, 4- or 5-fold more total ADAM12 mRNA as compared to unwounded tissue of the same type. In some embodiments, wound tissue that over-expresses an Adam12 gene product contains at least about 2-, 3-, 4- or 5-fold more total ADAM12 polypeptide as compared to unwounded tissue of the same type.

The nucleotide sequence of the human Adam12 gene can be obtained from public data bases (GENBANK Accession No. NC_000010.9). Two mRNA isoforms are illustrated in FIG. 1. The nucleotide and amino acid sequences of human ADAM12-L mRNA and polypeptides are illustrated in FIGS. 2A and 2B, respectively. Amino acids comprising the leader sequence of the pro-form of the ADAM12-L polypeptide ("pro-ADAM12-L" or "pro-ADAM12-L polypeptide") are underlined. The nucleotide and amino acid sequences of human ADAM12-S mRNA and polypeptide are illustrated in FIGS. 3A and 3B, respectively. Amino acids comprising the leader sequence of the pro-form of the ADAM12-S polypeptide ("pro-ADAM12-S" or "pro-ADAM12-S polypeptide") are underlined. In FIGS. 2A and 3A, the start codon is indicated in bold and underlined. In FIGS. 2B and 3B, the predicted cleavage site between the signal sequence and the pro-domain in the pro-ADAM12-L and pro-ADAM12-S forms is indicated with an arrowhead, the amino acid residues comprising the predicted mature ADAM12-L and ADAM12-S polypeptides and several predicted domains, (e.g., metalloprotease, disintegrin, cysteine-rich and transmembrane domains) are indicated, and the catalytic site is double-underlined.

Methods of determining amounts of mRNA gene expression products are well-known, and include by way of example and not limitation, microarray analyses (Brazma & Vilo, 2000, *FEBS Lett.* 480:17-24; Celis et al., 2000, *FEBS Lett.* 480:2-16), serial analysis of gene expression ("SAGE;" Madden et al., 2000, *Drug Discovery Today* 5:415-425), restriction enzyme amplification of digested cDNAs ("READS;" Prashar & Weissman, 1999, *Methods Enzymol.* 303:258-272), total gene expression analysis ("TOGA;" Sutcliffe et al., 2000, *Proc. Nat'l Acad. Sci. USA* 97:1976-81), expressed sequence tag sequencing (Celis et al., 2000, *FEBS Lett.* 480:2-16; Larsson et al., 2000, *J. Biotechnol.* 80:143-157), subtractive RNA fingerprinting ("SURF;" Fuchs et al., 2000, *Anal. Biochem.* 286:91-98; Larson et al., 2000, *Cytometry* 41:203-208), subtractive cloning differential display ("DD;" Jurecic & Belmont, 2000, *Curr. Opin. Microbiol.* 3:316-321), comparative genomic hybridization (Carulli et al., 1998, *J. Cell. Biochem. Supp.* 31:286-96) and quantitative real-time RT PCR ("A-Z of Quantitative PCR," Bustin, Ed., *INL Biotechnology Series*, International University Line, La Jolla, Calif. 2004). Reagents for carrying out these assays can be designed from the nucleotide sequences illustrated in FIGS. 2-3 using well-known, routine means. Specific reagents and methods of quantifying Adam12 gene transcription (mRNA) products via microarray analysis are described in Example 1. Specific probes and primers for quantifying Adam12 gene transcription (mRNA) products via quantitative real-time PCR are provided in a later section.

Methods of determining amounts of polypeptide expression gene products are well-known, and include by way of example and not limitation, protein arrays and proteomics (Celis et al., 2000, *FEBS. Lett.* 480:2-16; Jungblat et al., 1999, *Electrophoresis* 20:2100-2110), fluorescent in situ hybridization ("FISH;" Going & Guskerron, 1999, *Eur. J. Cancer* 35:1895-1904) and mass spectrometry (review in TO, 2000, *Comb. Chem. High Throughput Science.* 3:235-241; see also ITRAQ® product literature from *Applied Biosystems*). Reagents for carrying out these assays are either commercially available or can be designed from the ADAM12 polypeptide sequences illustrated in FIGS. 2 and 3 using well-known, routine means. Specific reagents and methods of quantifying Adam12 gene translation products (ADAM12 polypeptide) are described in Example 2. Anti-human ADAM12 antibody is described in (Kveiborg et al., 2005, *Cancer Res.,* 65(11):4754-4761).

The various methods and compositions described herein utilize ADAM12 inhibitory compounds. As used herein, an "ADAM12 inhibitory compound" is a compound that inhibits an activity of an ADAM12 polypeptide, or expression of an Adam12 gene product, such as for example synthesis of mRNA encoding an ADAM12 polypeptide (transcription) and/or synthesis of an ADAM12 polypeptide from ADAM12 mRNA (translation).

Compounds that inhibit an activity of an ADAM12 polypeptide can inhibit the protease activity of the metalloprotease domain of ADAM12-L and/or ADAM12-S. The chemical nature of the compounds can vary, and can range from small organic molecules, to small biological molecules such as peptides, hormones, oligonucleotides, to large biological molecules such as polypeptides, enzymes, antibodies and polynucleotides. It will be appreciated that this list is merely illustrative of representative types of ADAM12 inhibitory compounds that can be employed in the methods and compositions described herein, and is not intended to be limiting.

In some embodiments, the ADAM12 inhibitory compound inhibits the protease activity of the metalloprotease domain of an ADAM12 polypeptide. Such ADAM12 inhibitory compounds are known in the art, and include by way of example and not limitation, the class of inhibitors called "hydroxamate inhibitors," which specifically intersect in a bidentate manner via the hydroxyl and carbonyl oxygens of their hydroxamic group with the zinc ion in the catalytic site (Grams et al., 1995, *Biochem.* 34:14012-14020; Bode et al., 1994, *EMBO J.* 13:1263-1269).

Such hydroxymate inhibitors are typically composed of a carbon back-bone (See, e.g., WO 95/29892, WO 97/24117, WO 97/49679 and EP 0780386), a peptidyl back-bone (WO 9005719, WO 93/20047, WO 95/09841 and WO 96/06074) a peptidomimetic back-bone (Schwartz et al., 1992, *Progr. Med. Chem.* 29: 271-334; Rasmussen et al., 1997, *Pharmacol Ther.* 75:69-75; Denis et al., 1997, *Invest. New Drugs* 15:175-185). Alternatively, they contain a sulfonamide sulfonyl group which is bonded on one side to a phenyl ring and a sulfonamide nitrogen which is bonded to an hydroxamate group via a chain of one to four carbon atoms (See, e.g., EP 0757984).

Other peptide-based matrix metalloprotease inhibitors that can be used as ADAM12 inhibitory compounds in the methods described herein include thiol amides which exhibit collagenase inhibition activity (U.S. Pat. No. 4,595,700), N-carboxyalkyl derivatives containing a biphenylethylglycine which inhibit MMP-3, MMP-2 and collagenase (Durette, et al., WO 95/29689), lactam derivatives which inhibit matrix metalloproteases, TNF-alpha and aggrecanase (see U.S. Pat. No. 6,495,699), tricyclic sulfonamide compounds (see U.S. Pat. No. 6,492,422), the compound ONO-4817 (Ono Pharmaceutical Co. Ltd., Osaka, Japan; see also Mori, et al., 2002, *Anticancer Res.,* 22(6C):3985-8) and the collagenase inhibitors GM6001 (trade name Galardin) and GM1489 (a derivative of GM6001) (see U.S. Pat. No. 6,759,432). Specific examples of hydroxamic acid-based metalloprotease inhibitors include, but are not limited to, the compounds "5A" [NHOHCOCH$_2$CH(i-Bu)CO-tryptophan-NHMe], "21A" [NHOHCOCH$_2$CH(i-Bu)CO-tryptophan-NHCHMePh], "39A" [HOOCCH2CH(i-Bu)CO-tryptophan-NHCHMePh], "S1209" [NHOHCOCH2 CH(i-Bu)CO-tyrosine-OMeN-HMe], UL001 [HSCH$_2$CH(CH$_2$CH(CH$_3$)$_2$)CO-Phe-Ala-NH$_2$] and MP506 (Elastin Products Company, Inc.) (see U.S. Pat. Nos. 5,773,438 and 5,892,112).

Other compounds, such as KB-R7785, have also been reported to antagonize ADAM12 processing of HB-EGF (Asakura et al., 2002, *Nat. Med.* 8:35-40) and to act as inhibitors of ADAM12 (Oh et al., 2004, *Bioorg Med Chem. Lett.,* 14(24):6071-6074).

Recently, a mechanism-based matrix metalloprotease inhibitor, SB-3CT, was designed according to the X-ray crystallographic information of the MMP active site (Brown et al., 2000, *J. Am. Chem. Soc.,* 122:6799-6800). X-ray absorption studies revealed that binding of this molecule to the catalytic zinc reconstructs the conformational environment around the active site metal ion back to that of the pro-enzyme (Kleifeld et al., 2001, *J. Biol. Chem.* 276: 17125-17131). This SB-3CT compound is also expected to be useful as an ADAM12 inhibitory compound in the compositions and methods described herein.

Antibodies and antibody fragments capable of inhibiting the activity of matrix metalloproteases, and which are expected to be useful as ADAM12 inhibitory compounds in the compositions and methods described herein, are also known in the art. For example, one class of natural inhibitors is monoclonal antibodies. Several antibodies which may inhibit the activity of matrix metalloprotease have been raised against specific peptide sequences within the catalytic domain MMP-1 (Galvez et al., 2001, *J. Biol. Chem.* 276: 37491-37500). Antibodies directed against ADAM12 are also described in Kawaguchi et al., 2003, *J Cell Sci.* 116(19): 3893-904, incorporated herein by reference. Similarly, skilled artisans can raise antibodies against polypeptide sequences within the catalytic domain of ADAM12 to be used as ADAM12 inhibitory compounds.

The catalytic site of matrix metalloproteases includes a coordinated metal ion which becomes available for substrate binding following enzyme activation. Antibodies which recognize both electronic and structural determinants of the catalytic site have been reported to be potent inhibitors of matrix metalloproteases (See, for example, PCT Publication WO 04/087042).

Additional metalloprotease inhibitors expected to be useful as ADAM12 inhibitory compounds in the compositions and methods described herein include the various compounds disclosed in U.S. Pat. Nos. 6,500,847; 6,268,379; 5,968,795; 5,892,112; 5,872,152; 4,681,894; 4,943,587 and WO 06/014903, the disclosures of which are incorporated herein by reference.

Such ADAM12 inhibitory compounds will generally exhibit $IC_{50}$s of ADAM12 protease activity of less than about 1 mM, as measured in a standard in vitro inhibition assay, such as, for example the ADAM12 inhibition assay described by Horiuchi et al., (Horiuchi et al., 2007, *Mol Biol Cell*, 18:176-188), although ADAM12 inhibitory compounds that exhibit higher $IC_{50}$s may also find use in the methods and compositions described herein. In some embodiments, such ADAM12 inhibitory compounds will exhibit $IC_{50}$s in the range of 100 µM, 75 µM, 50 µM, 25 µM, 10 µM, 1 µM, 100 nM, 75 nM, 50 nM, 25 nM, 10 nM, 1 nM, or even lower. As will be appreciated by skilled artisans, in many contexts, ADAM12 inhibitory compounds having $IC_{50}$s in the micromolar, nanomolar or even subnanomolar range may be desirable.

The suitability of any compound that inhibits the metalloprotease activity of a matrix metalloprotease, including the above-described compounds for use as an ADAM12 inhibitory compound in the compositions and methods as described herein can be accessed in routine assays with ADAM12.

Animal models used to assay wound healing are well-known. Specific representative examples are taught in U.S. Pat. No. 7,060,795. For example, the healing rate of an ADAM12 inhibitory compound can be assessed by introducing the ADAM12 inhibitory compound into a wound and measuring whether the healing rate is altered by the presence of the inhibitor. The rate of wound healing in the presence and absence of an inhibitor can be determined. While any wound may be used, a wound model with predictable properties is desirable. Two animal chronic wound models commonly used are an ischemic rabbit ear model, and an induced diabetic rat model. Optimal epithelialization and wound healing may require some ADAM12 activity. Hence, the compositions and formulations provided herein do not necessarily promote maximal inhibition of ADAM12. Instead, the activity of the inhibitor formulation may be varied as needed to optimize epithelialization and wound healing, and may be varied according to whether the wound is a chronic or acute wound.

As will be recognized by skilled artisans, matrix metalloprotease inhibitors such as those described above may be "promiscuous" or "non-selective," in that they may inhibit more than one matrix metalloprotease. While such promiscuous or non-selective inhibitors having requisite activity against ADAM12 are expected to be useful in the compositions and methods described herein, in some embodiments, compounds that specifically or selectively inhibit the activity of ADAM12 are preferred. Compounds can be tested for any desired degree of specificity or selectively for ADAM12 using routine screening assays.

In some embodiments, the ADAM12 inhibitory compound is a compound that inhibits expression of an Adam12 gene product. Such ADAM12 inhibitory compounds can inhibit Adam12 gene expression by inhibiting the transcription of the Adam12 gene (i.e., by inhibiting synthesis of ADAM12 mRNA) and/or by inhibiting the translation of ADAM12 mRNA (i.e., by inhibiting synthesis of ADAM12 polypeptides). In some embodiments, such ADAM12 inhibitory compounds are oligonucleotides that are complementary to, or that specifically hybridize with, one or more nucleic acids encoding ADAM12, such as the Adam12 gene or ADAM12 mRNA. The hybridization of the oligonucleotide with the nucleic acid encoding ADAM12 interferes with the normal function of the encoding nucleic acid.

As used herein, "hybridization" means hydrogen bonding, which may be Watson-Crick, Hoogsteen or reversed Hoogsteen hydrogen bonding, between complementary nucleoside or nucleotide bases (nucleobases). For example, adenine and thymine are complementary nucleobases which pair through the formation of Watson-Crick hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise base pairing such that stable and specific binding occurs between the oligonucleotide and the DNA or RNA. It is understood in the art that the sequence of an oligonucleotide need not be 100% complementary to its target nucleic acid to be specifically hybridizable.

An antisense compound is specifically hybridizable when binding of the compound to a target DNA or RNA molecule interferes with the normal function of the target DNA or RNA to cause a loss of activity, and there is a sufficient degree of complementarity to avoid non-specific binding of the oligonucleotide compound to non-target sequences under conditions in which specific binding is desired, i.e., under physiological conditions in the case of in vivo assays or therapeutic treatment, and in the case of in vitro assays, under conditions in which the assays are performed.

Oligonucleotide compounds capable of specifically hybridizing to nucleic acids encoding polypeptides are well-known in the art, and include by way of example, and not limitation, antisense oligonucleotides, small interfering RNAs (siRNAs), micro RNA (miRNA), short hairpin RNAs (shRNAs) and antisense expression vectors. Antisense oligonucleotides, siRNA and miRNA capable of inhibiting expression of Adam12 gene products can be designed from the sequences of polynucleotides encoding ADAM12, such as the Adam12 gene and ADAM12 mRNA sequences illustrated in FIGS. 1-3, using principles that are well known in the art. For example, antisense ADAM12 inhibitory compounds can be designed from polynucleotide sequences encoding ADAM12 as described in Yagami-Hiromasa et al., *Nature*, 1995, 377:652-656; Abe et al., 1999, *Calcif. Tissue Int.* 64:508-515. siRNA ADAM12 inhibitory compounds can be designed from ADAM12 encoding polynucleotides as described in Cao et al., 2003, *Mol. Cell. Biol.* 123(19):6725-

6738. miRNA ADAM12 inhibitory compounds can be designed from ADAM12 encoding polynucleotides as described on several commercial websites (see, for example, world wide web at dharmacon.com). As will be recognized by skilled artisans, the lengths of such antisense, siRNA and miRNA molecules can vary, as can their degree of complementarity to the ADAM12 encoding polynucleotide. In some embodiments, antisense oligonucleotide ADAM12 inhibitory compounds will contain from 8-80, 8-70, 8-60, 8-50, 8-40, 8-35, 8-30, 8-25, 8-20, 8-15 or 8-10 nucleotides; siRNA ADAM12 will contain from 20 to 22 nucleotides; and miRNA ADAM12 inhibitory compounds will typically contain from 21 to 24 nucleotides. Oligonucleotide ADAM12 inhibitory compounds, including antisense, siRNA and miRNA oligonucleotides, need not exhibit 100% complementarity to the target region of the ADAM12-encoding nucleic acid to be effective in the methods and compositions described herein. Depending upon their length, oligonucleotides exhibiting between 80-100% complementarity are expected to be effective, although in some circumstances oligonucleotides having even lower percentages of complementarity will be effective. The only requirement is that the oligonucleotide be capable of specifically hybridizing to its target region of the ADAM12-encoding nucleic acid. The correlation between the length of an oligonucleotide, its degree or percentage of complementary to a target nucleic acid sequence and its ability to specifically hybridize to the target sequence under various different hybridization conditions is well understood (see, e.g., *Nucleic Acid Hybridization: A Practical Approach*, Haines & Higgins, Eds., IRL Press, Oxford, 1988). Oligonucleotide ADAM12 inhibitory compounds having the requisite degree of complementarity as a function of length to be useful in the methods and compositions described herein can be designed using these well-known principles.

In some embodiments, the oligonucleotide ADAM12 inhibitory compound is 90-100% complementary to a target region of ADAM12-encoding nucleic acid, with a degree of complementarity of greater than 95, 96, 97, 98 or 99% being preferred. In some embodiments the oligonucleotide ADAM12 inhibitory compound is 100% complementary ("completely complementary") to a target region of an ADAM12-encoding nucleic acid. Percentage of complementarity of an oligonucleotide to a region of a target nucleic acid can be determined routinely using basic sequence alignment search tools (BLAST programs; see, e.g., Altschul et al., 1990, *J. Mol. Biol.* 215:403-410; Zhang & Madden, 1997, *Genome Res.* 7:649-656).

The target region may be located in the untranslated region of the ADAM12-encoding nucleic acid or in the coding region, or may span the untranslated and coding regions. The targeted region can include the nucleic acid sequence surrounding the AUG start codon, which can include the AUG codon itself; sequences containing and/or surrounding the splice donor and/or acceptor sites in the introns of the Adam12 encoding unprocessed mRNA transcript; sequences containing and/or surrounding the splice donor and/or acceptor sites in the exons of the Adam12 unprocessed mRNA transcript; sequences spanning the intro-exon junctions of the unprocessed Adam 12 mRNA transcript; and the 3' untranslated regions of the Adam12 mRNA. In some embodiments, an Adam12 specific antisense oligonucleotide can target the splicing acceptor or donor regions to cause exon skipping, thereby inhibiting expression of the ADAM12 polypeptide. These approaches for inhibiting expression are described in, among others, U.S. Pat. No. 6,784,291; U.S. Pat. No. 6,210,892; U.S. Pat. No. 6,653,466; and U.S. patent publication 2002/0055481; all publications incorporated herein by reference.

A variety of different antisense oligonucleotides that can be used as ADAM12 inhibitory compounds in the methods and compositions described herein are also described in US 2004/0002467, published Jan. 1, 2004, the disclosure of which is incorporated herein by reference. Specific antisense oligonucleotides contemplated to be useful in the methods and compositions described herein are provided in TABLE 1 of US 2004/0002467 as SEQ ID NOS: 8-44, respectively. The nucleotide sequences of these oligonucleotides, as well as the specific antisense oligonucleotides containing these sequences described in Example 15 of US 2004/0002467, are incorporated herein by reference. The nucleotide sequences of these antisense oligonucleotides are reproduced below:

TABLE 1

| REGION | TARGET SEQ ID NO | TARGET SITE | SEQUENCE | % INHIB | SEQ ID NO |
|---|---|---|---|---|---|
| UTR | 4 | 4026 | ttgactagatctggttaatg | 77 | 8 |
| UTR | 4 | 4152 | ctacgaataatgatagcaga | 89 | 9 |
| UTR | 4 | 3776 | tttctatcaagcaccgcctt | 71 | 10 |
| UTR | 4 | 4265 | gttgcaagtgtttaagaaat | 94 | 11 |
| UTR | 4 | 3815 | tgctctagaaaggacagcga | 89 | 12 |
| UTR | 4 | 3399 | gactgctttccaataaggcc | 83 | 13 |
| UTR | 4 | 4541 | acactcagagtgaattatgt | 90 | 14 |
| UTR | 4 | 3174 | agcacagcacagcactgacg | 84 | 15 |
| Coding | 4 | 2514 | tcttatttgtaaacagcagt | 82 | 16 |
| UTR | 4 | 4689 | atactatgttgcctagatac | 87 | 17 |
| UTR | 4 | 3462 | gattctacttgggatctctt | 87 | 18 |
| UTR | 4 | 4818 | gctttacattttaaagaact | 92 | 19 |
| UTR | 4 | 4530 | gaattatgtaactgttgtca | 82 | 20 |
| UTR | 4 | 4340 | ccacatctcataatatttag | 30 | 21 |
| Coding | 4 | 2915 | ggtcctggccaaggcatgag | 93 | 22 |
| UTR | 4 | 4545 | taaaacactcagagtgaatt | 75 | 23 |
| UTR | 4 | 3502 | tggctctggcctgagatggg | 69 | 24 |
| UTR | 4 | 3230 | acattctgcataaattaata | 62 | 25 |
| UTR | 4 | 4570 | ttgacccaaaagaaggctt | 89 | 26 |
| UTR | 4 | 3733 | aaacatgctcacggctggtc | 93 | 27 |
| UTR | 4 | 4007 | ggttcacatctgaaaatagt | 85 | 28 |
| UTR | 4 | 4016 | ctggttaatggttcacatct | 93 | 29 |
| UTR | 4 | 3737 | ttccaaacatgctcacggct | 85 | 30 |
| UTR | 4 | 4870 | aatcagttacagtaattctg | 86 | 31 |
| UTR | 4 | 4617 | caagattcttggtacatatt | 87 | 32 |
| UTR | 4 | 4467 | atggcattttaccttatctg | 78 | 33 |
| UTR | 4 | 3844 | tcccaagctaaataacctac | 77 | 34 |
| UTR | 4 | 3328 | tcaagttcactaaaatacta | 37 | 35 |

TABLE 1-continued

| REGION | TARGET SEQ ID NO | TARGET SITE | SEQUENCE | % INHIB | SEQ ID NO |
|---|---|---|---|---|---|
| UTR | 4 | 4988 | atgccagatctaaggatttg | 81 | 36 |
| UTR | 4 | 4789 | tagaataaacagatgcatgc | 90 | 37 |
| Coding | 4 | 2843 | gtttggcttacaggtccct | 93 | 38 |
| UTR | 4 | 3643 | ctgtctgcaacccaggttct | 90 | 39 |
| UTR | 4 | 4419 | tcactttaaagaccttgtga | 69 | 40 |
| UTR | 4 | 4589 | tcaaagcataggaaaactgt | 83 | 41 |
| Coding | 4 | 2544 | gcacacaccttagtttttca | 44 | 42 |
| UTR | 4 | 3339 | agcaggatatttcaagttca | 74 | 43 |
| UTR | 4 | 4683 | tgttgcctagatacagtggg | 84 | 44 |

In TABLE 1, the numbers in the % inhibition column are the percentage inhibition data reported in the '2467 publication for the antisense oligonucleotides described in Example 15 of the '2467 publication.

As indicated in TABLE 1, SEQ. ID NOS:8-20, 22-34, 36-41 and 43-44 inhibited synthesis of human ADAM12 mRNA by at least 60% in quantitative real-time PCR experiments using the following PCR probes and primers:

```
Forward Primer:
                                       (SEQ. ID NO: 5)
GCTCCACAATATCCACACCAAGT Reverse Primer:
                                       (SEQ ID NO: 6)
TGAAAAAAGGTGTCGGCTTCTC Probe:
                                       (SEQ ID NO: 7)
FAM-CCCAGATCCACCCACACCGCCTATATTAA-TAMRA
``` as described in Examples 13-15 of US 2004/0002467, the disclosure of which is incorporated herein by reference.

In some embodiments, oligonucleotide ADAM12 inhibitory compounds have nucleotide sequences selected from SEQ. ID NOS:8-20, 22-34, 36-41 and 43-44.

In some embodiments, the oligonucleotide ADAM12 inhibitory compound will inhibit synthesis of ADAM12 mRNA by at least 70%, as measured in the quantitative real-time PCR assay described above. Specific examples of such ADAM12 inhibitory compounds include oligonucleotides having nucleotide sequences corresponding to SEQ ID NOS: 8-20, 22-23, 26-34, 36-39, 41 and 43-44.

In some embodiments, the oligonucleotide ADAM12 inhibitory compounds will inhibit synthesis of ADAM12 mRNA by at least 80%, as measured in the quantitative real-time PCR assay described above. Specific examples of such ADAM12 inhibitory compounds include oligonucleotides having sequences corresponding to SEQ ID NOS:9, 11-20, 22, 26-32, 36-39, 41 and 44.

In some embodiments, the ADAM12 inhibitory compound will inhibit synthesis of ADAM12 mRNA by at least 90%, as measured in the quantitative real-time PCR assay described above. Specific examples of such ADAM12 inhibitory compounds include oligonucleotides having nucleotide sequences corresponding to SEQ ID NOS:11, 14, 19, 22, 27, 29 and 37-39.

The sites or regions of the ADAM12-encoding nucleic acids to which oligonucleotide ADAM12 inhibitory compounds are complementary are referred to herein as "target sites" or "target regions." The nucleotide sequences of such target sites or target regions are referred to herein as "target sequences." The sequences of the target sites complementary to ADAM12 oligonucleotide inhibitory compounds having sequences corresponding to SEQ. ID NOS:8-20, 22-34, 36-41 and 43-44 are provided in TABLE 2, infra, as SEQ ID NOS: 45-78:

TABLE 2

| TARGET SITE | SEQUENCE | REV COMP OF SEQ ID | ACTIVE IN | SEQ ID NO |
|---|---|---|---|---|
| 4026 | cattaaccagatctagtcaa | 11 | H. sapiens | 45 |
| 4152 | tctgctatcattattcgtag | 12 | H. sapiens | 46 |
| 3776 | aaggcggtgcttgatagaaa | 13 | H. sapiens | 47 |
| 4265 | atttcttaaacacttgcaac | 14 | H. sapiens | 48 |
| 3815 | tcgctgtcctttctagagca | 15 | H. sapiens | 49 |
| 3399 | ggccttattggaaagcagtc | 16 | H. sapiens | 50 |
| 4541 | acataattcactctgagtgt | 17 | H. sapiens | 51 |
| 3174 | cgtcagtgctgtgctgtgct | 18 | H. sapiens | 52 |
| 2514 | actgctgtttacaaataaga | 19 | H. sapiens | 53 |
| 4689 | gtatctaggcaacatagtat | 20 | H. sapiens | 54 |
| 3462 | aagagatcccaagtagaatc | 21 | H. sapiens | 55 |
| 4818 | agttctttaaaatgtaaagc | 22 | H. sapiens | 56 |
| 4530 | tgacaacagttacataattc | 23 | H. sapiens | 57 |
| 2915 | ctcatgccttggccaggacc | 25 | H. sapiens | 58 |
| 4545 | aattcactctgagtgtttta | 26 | H. sapiens | 59 |
| 3502 | cccatctcaggccagagcca | 27 | H. sapiens | 60 |
| 3230 | tattaatttatgcagaatgt | 28 | H. sapiens | 61 |
| 4570 | aagccttcttttggggtcaa | 29 | H. sapiens | 62 |
| 3733 | gaccagccgtgagcatgttt | 30 | H. sapiens | 63 |
| 4007 | actattttcagatgtgaacc | 31 | H. sapiens | 64 |
| 4016 | agatgtgaaccattaaccag | 32 | H. sapiens | 65 |
| 3737 | agccgtgagcatgtttggaa | 33 | H. sapiens | 66 |
| 4870 | cagaattactgtaactgatt | 34 | H. sapiens | 67 |
| 4617 | aatatgtaccaagaatcttg | 35 | H. sapiens | 68 |
| 4467 | cagataaggtaaaatgccat | 36 | H. sapiens | 69 |
| 3844 | gtaggttatttagcttggga | 37 | H. sapiens | 70 |
| 4988 | caaatccttagatctggcat | 39 | H. sapiens | 71 |
| 4789 | gcatgcatctgtttattcta | 40 | H. sapiens | 72 |
| 2843 | aggggacctgtaagccaaac | 41 | H. sapiens | 73 |
| 3643 | agaacctgggttgcagacag | 42 | H. sapiens | 74 |
| 4419 | tcacaaggtctttaaagtga | 43 | H. sapiens | 75 |

TABLE 2-continued

| TARGET SITE | SEQUENCE | REV COMP OF SEQ ID | ACTIVE IN | SEQ ID NO |
|---|---|---|---|---|
| 4589 | acagttttcctatgctttga | 44 | H. sapiens | 76 |
| 3339 | tgaacttgaaatatcctgct | 46 | H. sapiens | 77 |
| 4683 | cccactgtatctaggcaaca | 47 | H. sapiens | 78 |

By virtue of the demonstrated inhibitory activity of their respective complementary oligonucleotides, these targets have been experimentally found to be "open to," and accessible for, hybridization with oligonucleotides. Those of skill will be able to design further embodiments of oligonucleotides capable of specifically hybridizing with these target sites to inhibit expression of ADAM12 using routine skill and experimentation. Accordingly, in some embodiments, the oligonucleotide ADAM12 inhibitory compound is an oligonucleotide capable of specifically hybridizing with a target sequence selected from SEQ ID NOS: 45-78 under physiological conditions.

Those of skill will also be able to identify additional target sites and sequences, and oligonucleotides capable of specifically hybridizing thereto, using routine skill and experimentation. Specific examples of antisense RNAs and siRNAs effective in reducing ADAM12 levels are described in Kawaguchi, supra; Lafuste et al., 2005, *Mol Biol Cell.* 16(2): 861-70; and Cao et al., 2003, *Mol Cell Biol.* 23(19):6725-6738.

As used herein, the expression "oligonucleotide" is intended to encompass not only oligoribonucleic acids and oligo 2'-deoxyribonucleic acids, that are composed of naturally occurring and/or encoding nucleotide bases ("nucleobases," e.g., adenine, guanine, thymine, cytocine and uracil) sugars and phosphate ester internucloside linkages, but also oligomers composed of one or more non-natural nucleobases, sugars and/or internucleoside linkages that retain their ability to specifically hybridize to a target site of an ADAM12-encoding nucleic acid. In some embodiments, such modified oligonucleotides are preferred over native forms owing to certain desirable properties, such as, for example, enhanced cellular uptake, enhanced affinity for the ADAM12-encoding nucleic acid under physiological or other conditions of use, and/or increased stability in the presence of degradatory enzyme, such as, for example, nucleases.

Representative examples of modified internucleoside linkages ("backbones") that include a phosphorous atom and that can comprise the oligonucleotide ADAM12 inhibitory compounds include, but are not limited to, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate, aminoalkylphosphoramidates, phosphorodiamidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5', or 2' to 2' linkage. In some embodiments, oligonucleotides having inverted polarity comprise a single 3' to 3' linkage at the 3'-most internucleotide linkage i.e., a single inverted nucleoside residue, which may be abasic (the nucleobase is missing or has a hydroxyl group in place thereof).

Methods of synthesizing oligonucleotides including one or more such modified internucleoside linkages are well-known. Specific representative methods are taught in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated herein by reference.

Representative examples of modified backbases that do not include a phosphorous atom and that comprise the oligonucleotide ADAM12 inhibitory compounds include, but are not limited to, oligonucleotides in which the backbone is formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Methods of synthesizing oligonucleotides including one or more such modified internucleoside linkages are well-known. Specific representative examples are taught in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference.

Representative examples of modified nucleobases that comprise the ADAM12 oligonucleotide inhibitory compounds include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin; 2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The*

*Concise Encyclopedia Of Polymer Science And Engineering*, pages 858-859, Kroschwitz, J. I., ed. John Wiley & Sons, 1990, those disclosed by Englisch et al., 1991, *Angewandte Chemie*, International Edition, 30:613, and those disclosed by Sanghvi Chapter 15, *Antisense Research and Applications*, pages 289-302, Crooke, S. T. and Lebleu, B. ed., CRC Press, 1993. Certain of these nucleobases are particularly useful for increasing the binding affinity of the oligonucleotide ADAM12 inhibitory compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-12° C. (Sanghvi, et al., ed., *Antisense Research and Applications*, CRC Press, Boca Raton, 1993, pp. 276-278) and in some embodiments are preferred base substitutions, especially when combined with 2'-O-methoxyethyl sugar modifications.

Methods of synthesizing oligonucleotides including one or more modified nucleobases are well-known. Specific representative examples are taught in U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, the disclosures of which are incorporated herein by reference.

Representative examples of modified sugars that can comprise the oligonucleotide ADAM12 inhibitory compounds include, but are not limited to, ribose that is substituted at the 2'-position with a group selected from OH, SH, $SCH_3$, OCN, CN, $CF_3$, $OCF_3$, $SOCH_3$, $SO_2CH_3$, $ONO_2$, $NO_2$, $N_3$, $NH_2$, Cl, Br, F, alkyl, O-alkyl, S-alkyl, NH-alkyl, alkenyl, O-alkenyl, S-alkenyl, NH-alkenyl, alkynyl, O-alkynyl, S-alkynyl, NH, alkynyl, O-alkyl-O-alkyl, alkyl, alkylaryl, O-alkylaryl, arylalkyl, O-arylalkyl, heterocycloalkyl, heterocycloalkylaryl, aminoalkylamino, polyalkylamino and substituted silyl where the alkyl group contains from 1-10 carbon atoms and the alkyl and alkynyl groups contain from 2-10 carbon atoms, and wherein the alkyl, alkenyl and alkynyl groups are optionally substituted. Specific examples of such 2'-substituent groups include, but are not limited to, $O[(CH_2)_nO]_mCH_3$, $O(CH_2)_nOCH_3$, $O(CH_2)_nNH_2$, $O(CH_2)_nCH_3$, $O(CH_2)_nONH_2$ and $O(CH_2)_nON(CH_2)_nCH_3]_2$, where n and m are each, independently of one another, integers ranging from 1 to 10; $OCH_2CH_2OCH_3$, also known as 2'-methoxyethoxy, 2'-O-(2-methoxyethyl) or 2'-MOE (Martin et al., 1995, *Helv. Chim. Acta.* 78:486-504); $OCH_2)_2ON(CH_3)_2$, also known as 2'-DMAOE; $OCH_2OCH_2N(CH_3)_2$, also known as 2'-dimethyl-aminoethoxyethoxy, 2'-O-dimethyl 1-amino-ethoxy-ethyl or 2'-DMAEOE); $OCH_3$; $OCH_2CH_2CH_2NH_2$; allyl $(CH_2CH=CH_2)$; O-allyl $(O-CH_2CH=CH_2)$; and F.

The 2'-modification may be in the arabino (up) position or the ribo (down) position.

Further representative examples of modified sugars that can comprise the oligonucleotide ADAM12 inhibitory compounds include ribose substituted at the 3'-position or 5'-position of the terminal nucleotide with groups such as those exemplified above for the 2'-position, 2'-5' linked ribose or deoxyribose sugars, cyclobutyl groups, etc.

Methods of synthesizing oligonucleotides including one or more such modified sugars are well-known. Specific representative examples are taught in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated herein by reference.

Another representative example of a modified sugar that can comprise the oligonucleotide ADAM12 inhibitory compound is ribose in which the 2'-hydroxyl group is linked to the 3' or 4'-position, thereby forming a bicyclic sugar. The linkage bridging the 2'-oxygen atom and the 3'- or 4'-carbon atom is typically an alkylene group, for example, containing one or two methylene moieties (e.g., $-CH_2-$ or $-CH_2CH_2-$). Oligonucleotides containing such bicyclic sugars are commonly referred to as locked nucleic acids or "LNAs." Methods for synthesizing LNAs are described in WO 98/39352 and WO 99/14226, the disclosures of which are incorporated herein by reference.

In some embodiments, modified oligonucleotides include compounds in which both the sugar and phosphate ester groups are replaced with non-sugar phosphate linkages (referred to herein as "oligonucleotide mimetics"). The nucleobases are retained for hybridization with the ADAM12-encoding nucleic acid. One representative example of such an oligonucleotide mimetic that has been shown to have excellent hybridization and other properties is referred to as a peptide nucleic acid ("PNA"). In PNAs, the sugar-phosphate backbone of an oligonucleotide is replaced with an amide containing backbone, the most common of which is an aminoethylglycine backbone (see, e.g., Nielsen et al., 1991, *Science* 254:1497-1500). Methods of synthesizing PNA compounds are described, for example, in U.S. Pat. Nos. 5,539,082; 5,714,331; and 5,719,262, the disclosures of which are incorporated herein by reference.

In some embodiments, oligonucleotide ADAM12 inhibitory compounds are oligonucleotides with phosphorothioate internucleosidic linkages, heteroatomic internucleosidic linkages or combinations thereof. Specific exemplary heteroatomic interlinkages include, but are not limited to, $-CH_2-NH-O-CH_2-$, $-CH_2-N(CH_3)-O-CH_3$-(known as a methylenene (methylimino) or MMI backbone, $-CH_2-O-N(CH_3)-CH_2-CH_2$, amides and morpholino. These internucleoside backbones, as well as methods of synthesizing oligonucleotides including them, are described, for example, in U.S. Pat. Nos. 5,489,677; 5,602,240; and 5,034,506, the disclosures of which are incorporated herein by reference.

Oligonucleotide ADAM12 inhibitory compounds can include one or more moieties or conjugates covalently bound to appropriate functional groups of the oligonucleotide moiety of the compound. Conjugate groups or moieties can be selected to impart the oligonucleotide ADAM12 inhibitory compound with specified properties as compared to an unconjugated oligonucleotide, such as, for example, cellular uptake, cellular distribution, cellular activity, pharmacokinetic activities, etc. Exemplary conjugating groups include, but are not limited to, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the disclosure of which is incorporated herein by reference. Conjugate moieties include but are not limited to lipid moieties such as a cholesterol moiety (Letsinger et al., 1989, *Proc. Natl. Acad. Sci. USA* 86:6553-6556), cholic acid (Manoharan et al., 1994, *Bioorg. Med. Chem. Let.* 4:1053-1060), a thioether, e.g., hexyl-S-tritylthiol (Manoharan et al., 1992, *Ann. N.Y. Acad. Sci.*, 660:306-309; Manoharan et al., 1993, *Bioorg. Med. Chem. Let.* 3:2765-2770), a thiocholesterol (Oberhauser et al., 1992, *Nucl. Acids Res.* 20:533-538), an aliphatic chain, e.g., dodecandiol or undecyl residues (Saison-Behmoaras et al., 1991, *EMBO J.* 10:1111-1118; Kabanov et al., 1990, *FEBS Lett.*, 259 327-330; Svinarchuk et al., 1993, *Biochimie* 75:49-54), a phospholipid, e.g., di-hexadecyl-rac-glycerol or triethyl-ammonium 1,2-di-O-hexadecyl-rac-gly-cero-3-H-phosphonate (Manoharan et al., 1995, *Tetrahedron Lett.*, 36:3651-3654; Shea et al., 1990, *Nucl Acids Res.* 18:3777-3783), a polyamine or a polyethylene glycol chain (Manoharan et al., 1995, *Nucleosides & Nucleotides* 14:969-973), or adamantane acetic acid (Manoharan et al., 1995, *Tetrahedron Lett.* 36:3651-3654), a palmityl moiety (Mishra et al., 1995, *Biochim. Biophys. Acta* 1264:229-237), or an octadecylamine or hexylamino-carbonyl-oxycholesterol moiety (Crooke et al., 1996, *J. Pharmacol. Exp. Ther.* 277, 923-937). Oligonucleotide ADAM12 inhibitory compounds may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, the disclosures of which are incorporated herein by reference.

It is not necessary for all positions in a given oligonucleotide ADAM12 inhibitory compound to be uniformly modified, and in fact more than one of the aforementioned modifications may be incorporated in a single compound or even at a single nucleoside within an oligonucleotide. The oligonucleotide ADAM12 inhibitory compounds also include oligonucleotides which are chimeric compounds. "Chimeric" oligonucleotides or "chimeras," in the context of this disclosure, are oligonucleotides that contain two or more chemically distinct regions, each made up of at least one monomer unit, i.e., a nucleotide in the case of an unmodified oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. The cleavage of RNA:RNA hybrids can, in like fashion, be accomplished through the actions of endoribonucleases, such as interferon-induced RNAseL which cleaves both cellular and viral RNA. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligonucleotides can be synthesized as composite structures of two or more oligonucleotides, modified oligonucleotides, oligonucleosides and/or oligonucleotide mimetics as described above. Such compounds have also been referred to in the art as hybrids or gapmers. Representative United States patents that teach the synthesis of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, the disclosures of which are incorporated herein by reference.

The oligonucleotide ADAM12 inhibitory compounds described herein may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Non-oligonucleotide ADAM12 inhibitory compounds described herein can likewise be synthesized using standard techniques. For example, small organic ADAM12 inhibitory compounds can be synthesized using standard techniques of organic chemistry. Protecting groups suitable for use in such syntheses are described, for example, in Greene & Wuts, "*Protective Groups in Organic Chemistry*," latest edition.

The ADAM12 inhibitory compounds may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, the disclosures of which are incorporated herein by reference.

The ADAM12 inhibitory compounds described herein encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the ADAM12 inhibitory compounds, compounds pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides ADAM12 inhibitory compounds described herein are prepared as SATE [(S-acetyl-2-thioethyl) phosphate] derivatives according to the methods disclosed in WO 93/24510 to Gosselin et al., or in WO 94/26764 and U.S. Pat. No. 5,770,713 to Imbach et al., the disclosures of which are incorporated herein by reference.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "1977, Pharmaceutical Salts," *J. of Pharma Sci.* 66:1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions described herein. These include organic or inorganic acid salts of the amines. In some embodiments, acid salts are hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotide ADAM12 inhibitory compounds, specific examples of pharmaceutically acceptable salts include, but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

When administered to patients as a therapeutic approach towards the treatment of and/or promotion of wound healing, the ADAM12 inhibitory compounds can be administered as the compound per se, or in the form of pharmaceutical compositions.

The compounds and/or pharmaceutical compositions may be administered in a number of ways depending upon whether local or systemic treatment is desired.

Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intrathecal or intraventricular, administration. Oligonucleotide ADAM12 inhibitory compounds with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). ADAM12 inhibitory compounds may be encapsulated within liposomes or may form complexes thereto, in particular to cationic liposomes. Alternatively, the compounds may be complexed to lipids, for example cationic lipids. Exemplary fatty acids and esters include but are not limited to, arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which the oligonucleotide is administered in conjunction with one or more penetration enhancers surfactants and chelators. Exemplary surfactants include fatty acids and/or esters or salts thereof, bile acids and/or salts thereof. Exemplary bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Exemplary fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylaza-cycloheptan-2-one, an acylcarnitine, an acylcholine, or a monoglyceride, a diglyceride or a pharmaceutically acceptable salt thereof (e.g. sodium). In some embodiments, oligonucleotide or other ADAM12 inhibitory compounds are administered with combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether.

ADAM12 inhibitory compounds may be delivered orally, in granular form including sprayed dried particles, or complexed to form micro or nanoparticles. For oligonucleotide ADAM12 inhibitory compounds, complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotide ADAM12 inhibitory compounds and their preparation are described in detail in U.S. application Ser. Nos. 08/886,829 (filed Jul. 1, 1997), 09/108,673 (filed Jul. 1, 1998), 09/256,515 (filed Feb. 23, 1999), 09/082,624 (filed May 21, 1998) and 09/315,298 (filed May 20, 1999), each of which is incorporated herein by reference in their entirety.

In some particularly convenient embodiments, the ADAM12 inhibitory compounds may usefully be incorporated into wound dressings for topical administration. Such dressings may be nonabsorbable or absorbable, air- and/or water-permeable, impermeable, or semipermeable, and may optionally effect controlled and/or sustained local release of the ADAM12 inhibitory compound contained therein. The wound dressings may include actives additional to one or more ADAM12 inhibitory compounds, such as antimicrobials and hemostatic agents.

Wound dressings comprising therapeutic actives suitable for use with ADAM12 inhibitory compounds are well-known.

For example, PCT Publication WO 07/024,972 discloses devices and methods for the treatment of wounds comprising an absorbent wound dressing material having non-leachable antimicrobial and anti-protease agents as well as a releasable antimicrobial agent and a releasable anti-protease agent that are ionically stabilized within the device so as to be released from the device in a controlled manner. PCT Publication WO 07/011,612 and US Patent Application publication No. 2007/0020320 disclose anti-microbial wound dressings comprising a water-soluble film-forming polymer carrier and a water-soluble glass-encapsulated anti-microbial agent that is embedded within the carrier and/or coated on a surface of the carrier, as well as methods of making said wound dressings. U.S. Patent Application publication No. 2007/0009586 discloses wound dressings with antimicrobial and elastase sequestration properties which provide enhanced wound fluid absorption, comprising a phosphorylated polysaccharide substrate complexed with at least one transition metal and an alginate coating.

Wound dressings suitable for delivery of ADAM12 inhibitory compounds to wounds include passive or activated matrices, which may be fully or partially conformable to a wound shape.

For example, ADAM12 inhibitory compounds may usefully be included within activated matrices, such as beads, microspheres, films, sponges, or wafers which may be used therapeutically by placement within the body. Such matrices may be used to coat surgical devices such as suture materials or implants. ADAM12 inhibitory compounds may be included within activated matrices such as those disclosed in U.S. Pat. No. 5,962,427, European Patent No. EP0892644, and European Patent Application EP 1510224, which disclose compositions in which a therapeutic agent, such as a nucleic acid encoding a protein of interest, is associated with or impregnated within a matrix to form a gene activated matrix. Once the gene activated matrix is prepared, it may be stored for future use or placed immediately at the site of the wound.

Matrices may include either biological or synthetic matrices, or combinations thereof. Biocompatible matrices may be formed from both natural or synthetic materials. In some embodiments, the matrices are non-biodegradable, for use in treatments in which it is clinically desirable to leave permanent structures in the body. In some embodiments, the matrices are biodegradable, for use in treatments in which the expression or elaboration of the ADAM12 inhibitory compound is desired for a short duration of time.

The matrices may take the form of sponges, implants, tubes, telfa pads, band-aids, bandages, pads, lyophilized components, gels, patches, powders or nanoparticles. In addition, matrices may usefully be designed to allow for sustained release of the ADAM12 inhibitory compounds over prolonged periods of time.

In embodiments in which the matrices are to be maintained in contact with the wound for extended periods of time, non-biodegradable matrices may be employed, such as sintered hydroxyapatite, bioglass, aluminates, other bioceramic materials and metal materials, such as titanium. A suitable ceramic delivery system is described in U.S. Pat. No. 4,596,574. The bioceramics may be altered in composition, such as in calcium-aluminate-phosphate; and they may be processed to modify particular physical and chemical characteristics, such as pore size, particle size, particle shape, and biodegradability. Polymeric matrices may also be employed, including acrylic ester polymers and lactic acid polymers, as disclosed in U.S. Pat. Nos. 4,521,909, and 4,563,489, respectively. Particular examples of useful polymers are those of orthoesters, anhydrides, propylene-cofumarates, or a polymer of one or more γ-hydroxy carboxylic acid monomers, e.g., γ-hydroxy auric acid (glycolic acid) and/or γ-hydroxy propionic acid (lactic acid).

Wound dressings suitable for delivery of ADAM12 inhibitory compounds may also take the form of compressible and noncompressible bandages, plasters, and patches as are well known.

For example, PCT Publication WO 07/002,696 describes decompressive thermogenic bandage for delivery of pharmacological compositions for treatment of tissue wounds via a permeable dermal patch positioned inside a self-adhering vessel having a one-way valve allowing evacuation of said vessel, wherein the dermal patch is impregnated with a heat activated pharmacological composition. Application of vacuum to the treated tissue disinfects the tissue while providing a bacterial infiltration barrier.

In embodiments in which the ADAM12 inhibitory compounds are to be used to promote healing of surgical wounds, the compound can be incorporated into, or onto, a suture, staple, or other device that will be used to close the wound. Drug-containing and/or coated sutures, staples and other devices that can be used at wound sites with routine modification to deliver locally ADAM12 inhibitory compounds are known in the art. Representative examples are described in US Patent Application Nos. 20070010856 and 20060182778, for example.

As will be appreciated by skilled artisans, ADAM12 inhibitory compounds that are biological in nature, for example, peptides, polypeptides, oligonucleotides and polynucleotides, can be administered as the inhibiting compound per se, or alternatively nucleic acids encoding such inhibitory compounds can be administered, and the inhibitory compound expressed, either by transcription or translation, in vivo. Methods for administering nucleic acids encoding entire therapeutic agents are well known, and are described, for example, in US Patent Application Nos. 20040086486 and 20020151516, the disclosures of which are incorporated herein by reference. Uptake of nucleic acids by mammalian cells may be enhanced using several known transfection techniques including the use of transfection agents. The formulation which is administered may contain such agents. Example of these agents include cationic agents (for example calcium phosphate and DEAE-dextran) and lipofectants (for example LIPOFECTAM™ and TRANSFECTAM™).

The amount of ADAM12 inhibitory compound administered will depend upon a variety of factors, such as the mode of administration, the activity of the compound, the height, age, weight and general condition etc., of the patient, the bioavailabilty of the compound, the type and/or location of the wound to be treated, and other criteria apparent to the treating physician. Typically, an amount of compound effective to achieve a desired level of ADAM12 inhibition in the wounded tissue will be administered. Initial dosages can be estimated initially from in vitro assays and adjusted for specific desired ADAM12 inhibitory compounds using routine methods. For example, an initial dosage for use in animals may be formulated to achieve a circulating blood or serum concentration of active compound that inhibits about 25% or more of ADAM12 activity, or a process associated therewith, such as keratinocyte migration, as measured in an in vitro assay. Alternatively, an initial dosage for use in animals may be formulated to achieve a circulating blood or serum concentration of active compound that is equal to or greater than the $IC_{50}$ as measured in an in vitro assay. A suitable dose may be from 0.1 to 100 mg/kg body weight such as 1 to 40 mg/kg body weight. Calculating dosages to achieve such circulating blood or serum concentrations taking into account the bioavailability of the particular active compound is well within the capabilities of skilled artisans. For guidance, the reader is referred to Fingl & Woodbury, "General Principles," *In: The Pharmaceutical Basis of Therapeutics*, Chapter 1, pp. 1-46, 1975, and the references cited therein.

EXAMPLES

The working examples that follow, which are intended to be illustrative and not limiting, highlight various features of the invention(s) described herein.

Example 1

ADAM12 mRNA is Up-Regulated in Chronic Skin Ulcers

Preparation of Samples. Chronic Wound Skin Biopsies were Obtained from Discarded tissue after debridement procedures on three consenting patients with venous reflux ulcers (approved protocol 01-0960(001) 03sux). A small portion of the specimens were fixed in formalin and processed for paraffin embedding, whereas the majority of the samples were stored in RNAlater (Ambion) for subsequent RNA isolation. Normal skin specimens were obtained as discarded tissue from voluntary surgery (approved protocol 25121).

Hybridization of Probes. Samples stored in RNAlater were homogenized and total RNA isolated using RNeasy Mini Kit (Qiagen, Valencia, Calif.) according to the manufacturer's protocol. Approximately 5 µg of total RNA was reverse transcribed and amplified as described (Stojadinovic et al., 2007, *J. Biol. Chem.* 282:4021-4034). The cRNA probe was biotinylated using the Affymetrix ENZO BioArray HighYield RNA Transcript Labeling Kit, and labeled cRNA was hybridized to HG-U133A arrays (more than 22000 probe sets) (Affymetrix, Santa Clara, Calif.). The arrays were washed, stained with avidin-biotin-streptavidin-phycoerythin labeled antibody using an Affymetrix fluidics station and then scanned using an Agilent GeneArray Scanner system (Hewlett-Packard, Palo Alto, Calif.) as described by Affymetrix.

Data Analysis. Microarray Suite 5.0 (Affymetrix) was used for data extraction and for further analysis, data mining tool 3.0 (Affymetrix, Santa Clara, Calif.) and GeneSpring™ software 7.3.1 (Silicon Genetics, Redwood City, Calif.) were used for normalization, fold change and p-value calculations. Statistical comparisons of expression level, between test and control samples were performed using ANOVA test. Only genes with a p-value of less than 0.05 were considered to be statistically significant. Differential expressions of transcripts were determined by calculating the fold change. Genes were considered regulated if the expression levels differed more than 2-fold relative to normal skin.

Results. To determine which molecules play a role in pathogenesis of wound healing we utilized biopsies from patients with chronic ulcers and compared their expression profiles with those of normal human skin using microarray technology, as described above. Different samples were compared and a specific transcriptional profile was obtained. To determine statistically significant changes in gene expression levels between chronic ulcers and normal human skin, statistical analyses were performed using volcano plot software and only a subset of genes that demonstrate statistical significance (p value<0.05) selected. Using a two-fold difference in expression as a cut-off value, 557 genes were found to be differentially regulated between normal skin and non-healing edges from chronic wounds. Expression of ADAM12 was found to be approximately 5-fold greater in biopsy samples of chronic skin ulcers from all three patients, as compared to normal skin, with the average being 5.88.

Example 2

ADAM12 is Up-Regulated in Chronic Skin Ulcers

Protocol. Seven micrometer thick sections from the paraffin-embedded skin samples from three patients described in Example 1 (using three replicates from each patient) were cut and stained overnight with anti-ADAM12 antibody (rb122) at 1:100 dilution (generous gift of Dr. Wewer U. M.; for description, see Kveiborg et al., 2005, *Cancer Res.*, 65(11):4754-4761) using Vectastain ABC Elite Universal Kit (Vector Labs) as previously described (Wang et al., 2002, *J. Biol. Chem.* 277:26573-26580). Unwounded skin from the same patients was used as a negative control. All negative controls were prepared by substitution of the primary antibody with PBS. Staining was analyzed using Nikon Eclipse E800 microscope and digital images were collected using SPOT-Camera Advanced program.

Figure 4A:
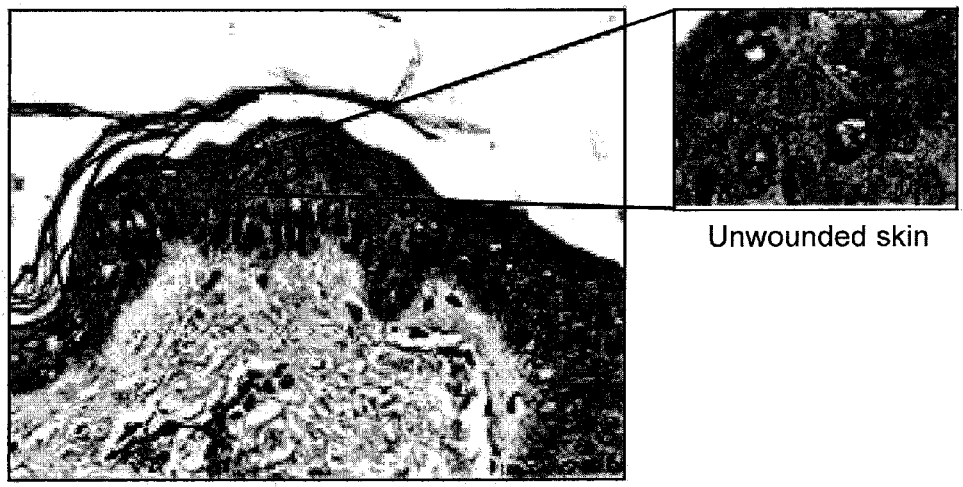
FIG. 4 provides photographs of biopsies taken from unwounded skin (FIG. 4A) and the non-healing edge of chronic skin ulcers (FIG. 4B) that were stained with a labeled antibody specific for ADAM12.
Figure 4B:
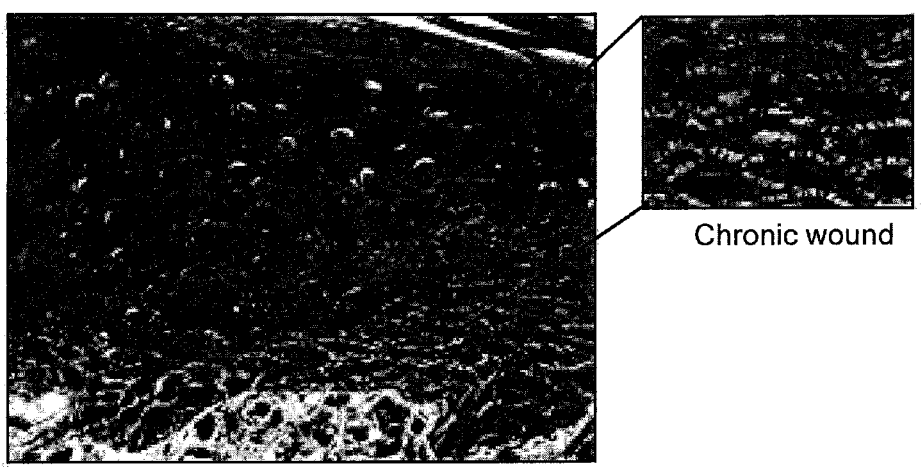

Results. Photographs of exemplary stained normal and chronic wound tissue are provided in FIG. 4. As expected, ADAM12 was observed in both the cytoplasm and membrane of the epidermis of normal skin (FIG. 4A). A robust increase in ADAM12 was observed in biopsies originating from the non-healing edge of chronic ulcers was observed, confirming the microarray data of Example 1 (FIG. 4B). Membranous staining was patchy and present throughout the epidermis in chronic wound samples, while in normal skin, membranous staining was continuous throughout the membrane, but present only on the membrane surrounding small number of keratinocytes.

These data, along with those of Example 1, confirm that expression of ADAM12 is induced in chronic wounds.

Example 3

ADAM12 Inhibits Migration of Keratinocytes in Chronic Skin Ulcers

Generation of ADAM12 knock-out mice ("ADAM12KO") and wildtype (WT) littermates. Two male and two female ADAM12+/− mice (Kurisaki et al., 2003, *Mol. Cell. Biol.* 23; 55-61) were mated in two separate cages, producing litters of between 5 and 7 pups in each cage. ADAM12KO and WT littermate mice were maintained in an accredited animal facility (at the Hospital for Special Surgery) according to the guidelines of the American Veterinary association, and all experiments were approved by the HSS Institutional Animal Care and Use Committee. Each mating cage littered mice within 24-36 hours of each other, producing mice of similar age when used for experimental analysis. A total of four litters were produced. All littered mice were sacrificed and their tails used for genotype analysis by southern blotting to determine ADAM12+/+ (WT) and ADAM12KO. A total of 25 newborn pups were sacrificed with genotypes as follows: 7 ADAM12KO, 6 ADAM12+/+, 12 ADAM12+/−. Among these, the wild type and ADAM12KO mice were selected for further experimental analysis. Five ADAM12KO pups and five WT littermates were littered from cage 1 and two ADAM12KO and 1 WT were littered from cage 2.

Explant Wound Healing Assay. Skin explants were prepared from 1 day old pups as described (Mazzalupo et al., 2003, *Dev. Dyn.* 226:356-65). Briefly, one day old mice were sacrificed and washed in a 10% povidine/iodine solution and rinsed in phosphate buffered saline (PBS). The epidermis, dermis, and underlying adipose tissue and fascia were completely removed from the body of the animal by incision on the ventral aspect of the specimen and careful dissection over the dorsal aspect. The adipose tissue/fascia was removed in order to insure adherence of the dermis directly to the plate. The tissue specimen was once again washed in 10% povidine/iodine solution followed by phosphate-buttered saline ("PBS"). Six 3-mm full thickness biopsies were taken from the dorsal midline of each animal and plated individually in 24 well plates. Each sample was submerged in 200 μL of nutrient-rich media containing adenine (24.4 μg/ml), insulin (5 μg/mL), transferrin (5 μg/mL), hydrocortisone (0.4 mM), 10% fetal calf serum, cholera toxin (0.5 μg/ml), penicillin G (100 IU/mL), T3 (1 mM), gentamicin (25 μg/mL), 75% Dublecco's Modified Eagle's Medium, and 25% F-12 nutrient mixture (GIBCO™, Invitrogen cell culture, Carlsbad, Calif.). For additional stimulation of proliferation/migration, three of the six samples from each mouse were treated with epidermal growth factor ("EGF") (25 μg/mL) and the other three were left untreated. Samples were incubated overnight at 37° C. and, the following day, media was replaced with 1.5 mL of fresh media and EGF samples were re-treated. Keratinocyte migration was observed over the course of 7 days, with changing of media on days 1, 3, and 5.

To document the keratinocyte migration front, pictures were taken on days 3, 5, and 7 using a Nikon Coolpix 35 mm camera with manual zoom mounted on a Nikon Eclipse TS100 inverted microscope. The objective was a Plan-UW 2x/0.06 (Nikon, Inc.), and the software used to process images was Picasa 2.0 (Microsoft).

Figure 6:
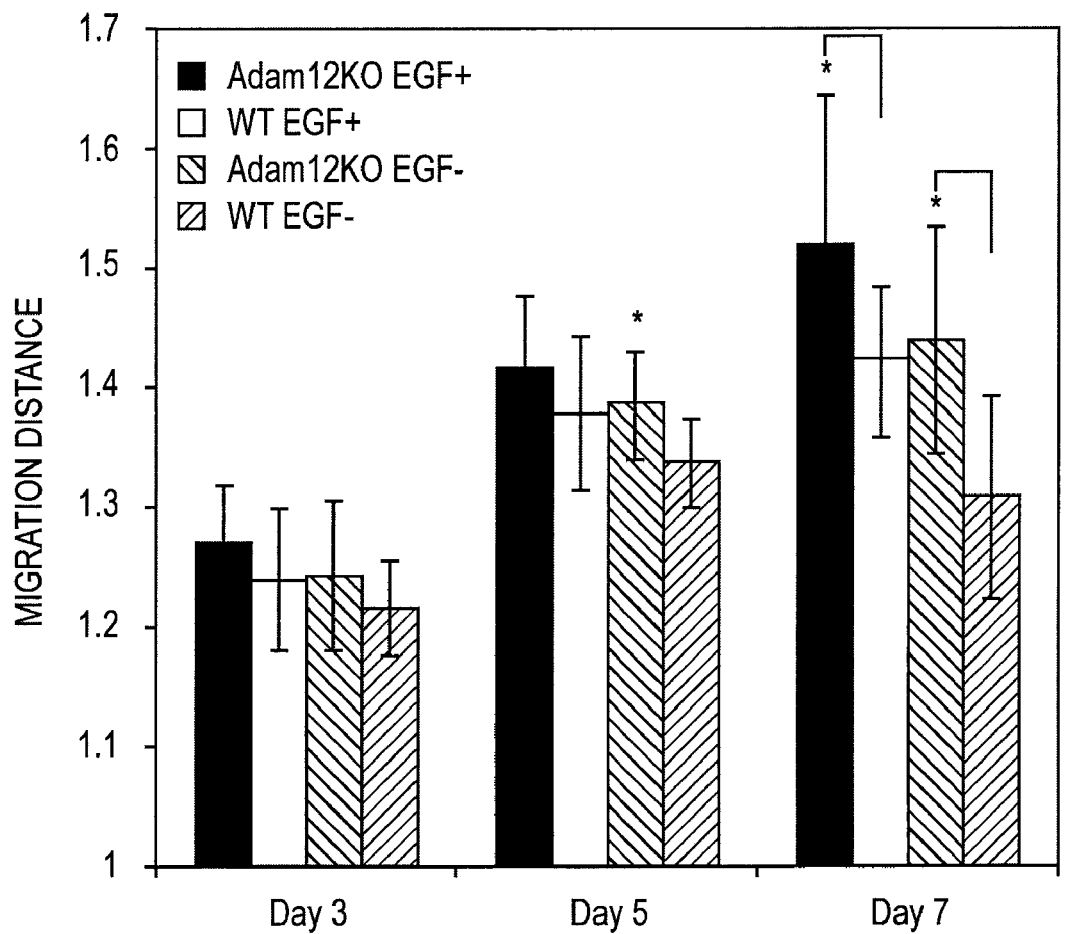
FIG. 6 provides a graph illustrating average keratinocyte migration distance observed as a function of time in skin explants taken from ADAM12 knockout (ADAM12KO) and wild type (WT) mice that were either treated (EGF+) or untreated (EGF−) with epidermal growth factor.

Pictures taken on days 3, 5, and 7 were used for data analysis. Each experiment was performed in triplicate and migration, and each photograph was assessed and quantified by two different people, each measuring independently, and each blinded to the source of the photograph. The distance of keratinocyte migration was calculated using the image program, ImageJ (NIH). Briefly, the center of the punch biopsy was determined and all other measurements were made from that point, and all measurements were normalized to length of the radius of the biopsy. Using the line tool, an average of 10 line measurements per sample were taken from the center point to the periphery of the punch biopsy in the areas of furthest cell migration. An average of the measurement from the center point to the edge of the greatest confluent cell migration was calculated from the 12 line measurements taken from each sample. Measurements were carried out in this manner (i.e., center to punch biopsy edge and center to keratinocyte migration front) in order to account for the differences in manual zoom of the pictures, which would overestimate or underestimate the migration distance. The values measured from the center point to the edge of the punch biopsy were averaged to give the average radius of the biopsy. The values measured from the center point to the edge of confluent cell migration were averaged to give the average radial distance of cell migration. The values charted in FIG. 6 (described below) are migration distance calculated from the center of the biopsy to biopsy radius. A total of 11 wild type EGF treated, 10 wild type untreated, 16 ADAM12KO EGF treated, and 18 ADAM12KO untreated biopsies were included in statistical analysis using Student's t-test available at http://www.physics.csbsju.edu/. P values of less than 0.05 were considered statistically significant.

After 7 days of migration the punch biopsies were removed from the wells and the remaining adherent cells washed with PBS and fixed for 10 minutes in methanol at −4° C. Following fixation, cells were washed with PBS and permeabilized with 0.1% Triton X-100 in PBS for 10 minutes at room temperature. Cells were then washed in PBS and incubated in 5% BSA in PBS (1-2 ml) for 30 min. Cells were incubated overnight in 200 μl/well of rabbit polyclonal antibody detecting human K17 (1:1000) (a gift from Dr Coulombe) (McGowan & Coulombe, 1998, *J. Cell. Biol.* 143:469-86) diluted in 5% BSA in 1×PBS. Slides were then rinsed in PBS and incubated with secondary fluorescent-conjugated anti-rabbit IgG antibody (diluted as 1:160)(Sigma-Aldrich) for three hours at room temperature (50 μL). After a final wash in PBS the stained slides were examined under a Carl Zeiss microscope and digital images collected using Adobe Photoshop 4.0 TWAIN 32 program.

Figure 5:
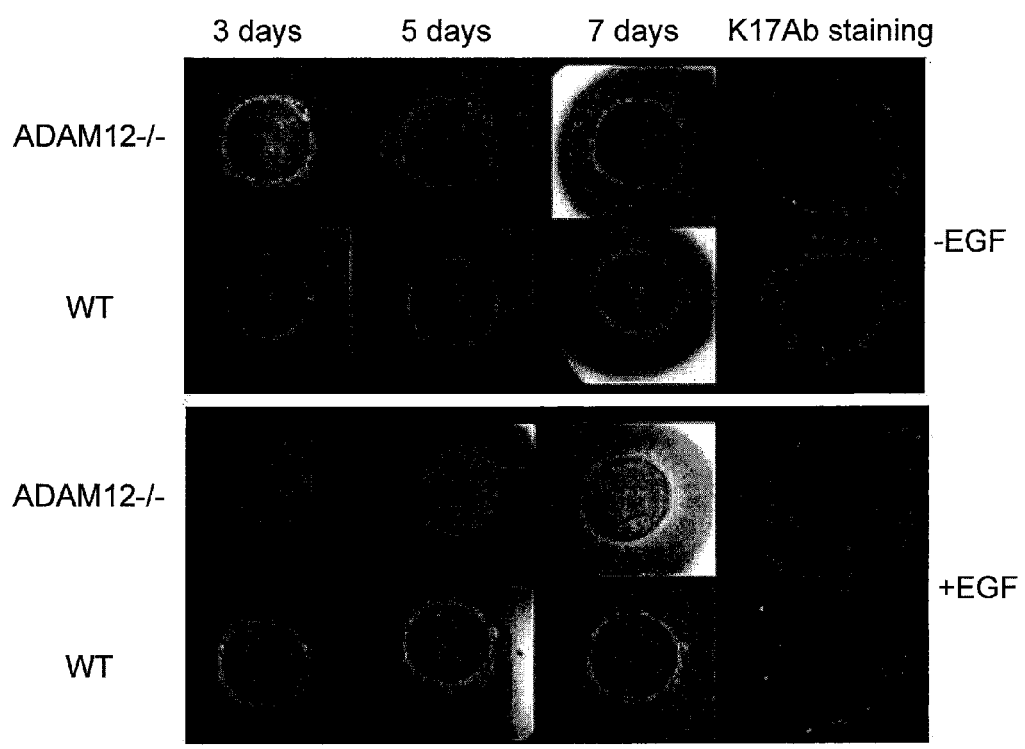
FIG. 5 provides photographs of skin explants from ADAM12 knockout (ADAM12−/−) and wild type (WT) mice that were either treated (+EGF) or untreated (−EGF) with epidermal growth factor.

Results. To functionally evaluate the role of ADAM12 in wound healing we used an established explant wound healing model in ADAM12 knockout mice (see Mahajan, et al., 2004, *Mol. Cell. Biol.* 24, 4994-5004). Ex vivo cultures of skin explants from wild type pups and their ADAM12 −/− littermates were compared over a period of seven days. We measured and quantified keratinocyte migration for triplicate explants of all the pups from a total of four litters (from two cages) and found a significant increase in migratory capacity as well as response to EGF in the ADAM12KO mice when compared to WT controls. In all, we tested 78 explants from ADAM12KO mice in 5 separate trials. Thirty-four of these were tested on two separate trials in parallel with their wild-type littermates. On all occasions a significant increase in migration compared to wild type was observed. As expected, keratinocytes derived from WT mouse explants migrated out, and moved steadily during a seven day period (FIG. 5). When stimulated with EGF these keratinocytes responded with enhanced proliferation and migration. Interestingly, keratinocytes from explants derived from ADAM12KO pups showed a significant (p=0.0014) increase in migration compared to WT controls. Furthermore, additional stimulation by EGF also resulted in a significant increase in migration (p=0.026) in ADAM12KO skin explants, as compared to WT controls.

Lastly, we used a K17 specific antibody to test the origin of the migratory cells. Almost the entire cell population that migrated out of the explant was K17 positive (FIG. 5, panel labeled "K17Ab staining"), thus confirming that migratory cells are indeed keratinocytes.

To evaluate these findings in other members of the family of ADAMs we performed similar analyses using different mice backgrounds including ADAM 8 −/−, ADAM 9 −/−, ADAM15 −/−, ADAM17 −/−, ADAM19 −/−, ADAM9 −/− ADAM15 −/− double knockout, ADAM9 −/− ADAM12 −/− ADAM15 −/− triple knockout. ADAM9 −/−, ADAM17 −/−, ADAM 19 −/− showed no increase in migration compared to wildtype (data not shown). Interestingly, ADAM8 −/− showed a dramatic reduction in keratinocyte outgrowth. These experiments were repeated on two separate occasions using the same method and analyses presented above. Taken together, we found that only ADAM12KO mice exhibit enhanced capacity of keratinocyte migration and better response to EGF stimulation, suggesting that inhibition of ADAM12 may promote epithelialization and wound healing by promoting the migration of keratinoctyes.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of promoting healing of a chronic wound, comprising:
   administering to the wound an amount of a selective ADAM12 inhibitory compound effective to promote healing of the wound,
   in which the ADAM12 inhibitory compound inhibits expression of mRNA encoding ADAM12.

2. The method of claim 1 in which the ADAM12 inhibitory compound is an antisense oligonucleotide, an iRNA, an siRNA, or a nucleic acid encoding an antisense oligonucleotide, an iRNA or an siRNA.

3. The method of claim 1 or claim 2 in which the ADAM12 inhibitory compound is administered locally to the wound.

4. The method of claim 3 in which the ADAM12 inhibitory compound is included in a dressing that is applied topically to the wound.

5. The method of claim 3 in which the ADAM12 inhibitory compound is administered locally to the wound via injection.

6. The method of claim 2 in which the ADAM12 inhibitor compound is an antisense oligonucleotide.

7. The method of claim 2 in which the ADAM12 inhibitor compound is a siRNA.

8. A method of promoting healing of a chronic wound, comprising:
   administering to the wound an amount of a selective ADAM12 inhibitory compound effective to promote healing of the wound,
   in which the ADAM12 inhibitor compound is an antibody.

9. The method of claim 8, wherein the antibody is administered locally to the wound.

10. The method of claim 9, wherein the antibody is administered locally to the wound via injection.

11. The method of claim 8, wherein the antibody is administered topically to the wound.

12. The method of claim 11 in which the antibody is included in a dressing that is applied topically to the wound.

13. The method of claim 1 or claim 8, wherein the chronic wound is an arterial ulcer, a diabetic foot ulcer or a venous ulcer.

* * * * *

SEQUENCE LISTING

```
<160> NUMBER OF SEQ ID NOS: 78

<210> SEQ ID NO 1
<211> LENGTH: 5504
<212> TYPE: DNA
<213> ORGANISM: Homo sapiens

<400> SEQUENCE: 1
gactgctggc cgtggatcca tttcacaggc ctgccttctc tcactaacgc tcttcctagt      60
ccccgggcca actcggacag tttgctcatt tattgcaacg gtcaaggctg gcttgtgcca     120
gaacggcgcg cgcgcgcgca cgcacgcaca cacacggggg gaaactttt taaaaatgaa     180 aggctagaag agctcagcgg cggcgcgggc gctgcgcgag ggctccggag ctgactcgcc     240
gaggcaggaa atccctccgg tcgcgacgcc cggcccggc tcggcgcccg cgtgggatgg      300
tgcagcgctc gccgccgggc ccgagagctg ctgcactgaa ggccggcgac gatggcagcg     360
cgcccgctgc ccgtgtcccc cgcccgcgcc ctcctgctcg ccctggccgg tgctctgctc     420
gcgccctgcg aggcccgagg ggtgagctta tggaaccaag gaagagctga tgaagttgtc     480
agtgcctctg ttgggagtgg ggacctctgg atcccagtga agagcttcga ctccaagaat     540
catccagaag tgctgaatat tcgactacaa cgggaaagca aagaactgat cataaatctg     600
```

```
gaaagaaatg aaggtctcat tgccagcagt tcacggaaa cccactatct gcaagacggt      660
actgatgtct ccctcgctcg aaattacacg gtaattctgg gtcactgtta ctaccatgga     720
catgtacggg gatattctga ttcagcagtc agtctcagca cgtgttctgg tctcagggga     780
cttattgtgt ttgaaaatga aagctatgtc ttagaaccaa tgaaaagtgc aaccaacaga     840
tacaaactct tcccagcgaa gaagctgaaa agcgtccggg gatcatgtgg atcacatcac     900
aacacaccaa acctcgctgc aaagaatgtg tttccaccac cctctcagac atgggcaaga     960
aggcataaaa gagagaccct caaggcaact aagtatgtgg agctggtgat cgtggcagac    1020
aaccgagagt ttcagaggca aggaaaagat ctggaaaaag ttaagcagcg attaatagag    1080
attgctaatc acgttgacaa gttttacaga ccactgaaca ttcggatcgt gttggtaggc    1140
gtggaagtgt ggaatgacat ggacaaatgc tctgtaagtc aggacccatt caccagcctc    1200
catgaatttc tggactggag gaagatgaag cttctacctc gcaaatccca tgacaatgcg    1260
cagcttgtca gtggggttta tttccaaggg accaccatcg gcatggcccc aatcatgagc    1320
atgtgcacgg cagaccagtc tgggggaatt gtcatggacc attcagacaa tccccttggt    1380
gcagccgtga ccctggcaca tgagctgggc cacaatttcg ggatgaatca tgacacactg    1440
gacaggggct gtagctgtca aatggcggtt gagaaaggag gctgcatcat gaacgcttcc    1500
accgggtacc catttcccat ggtgttcagc agttgcagca ggaaggactt ggagaccagc    1560
ctggagaaag gaatgggggt gtgcctgttt aacctgccgg aagtcaggga gtctttcggg    1620
ggccagaagt gtgggaacag atttgtgaa gaaggagagg agtgtgactg tggggagcca    1680
gaggaatgta tgaatcgctg ctgcaatgcc accacctgta ccctgaagcc ggacgctgtg    1740
tgcgcacatg ggctgtgctg tgaagactgc cagctgaagc ctgcaggaac agcgtgcagg    1800
gactccagca actcctgtga cctcccagag ttctgcacag gggccagccc tcactgccca    1860
gccaacgtgt acctgcacga tgggcactca tgtcaggatg tggacggcta ctgctacaat    1920
ggcatctgcc agactcacga gcagcagtgt gtcacgctct ggggaccagg tgctaaacct    1980
gcccctggga tctgctttga gagagtcaat tctgcaggtg atccttatgg caactgtggc    2040
aaagtctcga agagttcctt tgccaaatgc gagatgagag atgctaaatg tggaaaaatc    2100
cagtgtcaag gaggtgccag ccggccagtc attggtacca atgccgtttc catagaaaca    2160
aacatccccc tgcagcaagg aggccggatt ctgtgccggg ggacccacgt gtacttgggc    2220
gatgacatgc cggacccagg gcttgtgctt gcaggcacaa agtgtgcaga tggaaaaatc    2280
tgcctgaatc gtcaatgtca aaatattagt gtctttgggg ttcacgagtg tgcaatgcag    2340
tgccacggca gagggtgtg caacaacagg aagaactgcc actgcgaggc ccactgggca    2400
cctcccttct gtgacaagtt tggctttgga ggaagcacag acagcggccc catccggcaa    2460
gcagataacc aaggtttaac cataggaatt ctggtgacca tcctgtgtct tcttgctgcc    2520
ggatttgtgg tttatctcaa aaggaagacc ttgatacgac tgctgtttac aaataagaag    2580
accaccattg aaaaactaag gtgtgtgcgc ccttcccggc caccccgtgg cttccaaccc    2640
tgtcaggctc acctcggcca ccttggaaaa ggcctgatga ggaagccgcc agattcctac    2700
ccaccgaagg acaatcccag gagattgctg cagtgtcaga atgttgacat cagcagaccc    2760
ctcaacggcc tgaatgtccc tcagcccag tcaactcagc gagtgcttcc tccccctccac    2820 cgggccccac gtgcacctag cgtccctgcc agaccctgc cagccaagcc tgcacttagg    2880
caggcccagg ggacctgtaa gccaaacccc cctcagaagc tctgcctgc agatcctctg    2940 gccagaacaa ctcggctcac tcatgccttg gccaggaccc caggacaatg ggagactggg    3000
```

```
ctccgcctgg cacccctcag acctgctcca caatatccac accaagtgcc cagatccacc    3060
cacaccgcct atattaagtg agaagccgac accttttttc aacagtgaag acagaagttt    3120
gcactatctt tcagctccag ttggagtttt ttgtaccaac ttttaggatt ttttttaatg    3180
tttaaaacat cattactata agaactttga gctactgccg tcagtgctgt gctgtgctat    3240
ggtgctctgt ctacttgctc aggtacttgt aaattattaa tttatgcaga atgttgatta    3300
cagtgcagtg cgctgtagta ggcatttttta ccatcactga gttttccatg gcaggaaggc    3360
ttgttgtgct tttagtattt tagtgaactt gaaatatcct gcttgatggg attctggaca    3420
ggatgtgttt gctttctgat caaggcctta ttggaaagca gtccccaac taccccagc     3480 tgtgcttatg gtaccagatg cagctcaaga gatcccaagt agaatctcag ttgattttct    3540
ggattcccca tctcaggcca gagccaaggg gcttcaggtc caggctgtgt ttggctttca    3600
gggaggccct gtgccccttg caactggagg gcaggctcc cagggacacc tgggagaaat     3660
ctggcttctg gccaggaagc tttggtgaga acctgggttg cagacaggaa tcttaaggtg    3720
tagccacacc aggatagaga ctggaacact agacaagcca gaacttgacc ctgagctgac    3780
cagccgtgag catgtttgga aggggtctgt agtgtcactc aaggcggtgc ttgatagaaa    3840
tgccaagcac ttcttttttct cgctgtcctt tctagagcac tgccaccagt aggttattta    3900
gcttgggaaa ggtggtgttt ctgtaagaaa cctactgccc aggcactgca aaccgccacc    3960
tccctatact gcttggagct gagcaaatca ccacaaactg taatacaatg atcctgtatt    4020
cagacagatg aggcttttcca tgggaccaca actatttcca gatgtgaacc attaaccaga    4080
tctagtcaat caagtctgtt tactgcaagg ttcaacttat taacaattag gcagactctt    4140
tatgcttgca aaactacaa ccaatggaat gtgatgttca tgggtatagt tcatgtctgc     4200
tatcattatt cgtagatatt ggacaaagaa ccttctctat ggggcatcct cttttttccaa   4260 cttggctgca ggaatcttta aaagatgctt ttaacagagt ctgaacctat tcttaaaca    4320 cttgcaacct acctgttgag catcacagaa tgtgataagg aaatcaactt gcttatcaac    4380
ttcctaaata ttatgagatg ctggcttggg cagcatcccc ttgaactctt cactcttcaa    4440
atgcctgact agggagccat gtttcacaag gtctttaaag tgactaatgg catgagaaat    4500
acaaaaatac tcagataagg taaaatgcca tgatgcctct gtcttctgga ctggttttca    4560
cattagaaga caattgacaa cagttacata attcactctg agtgttttat gagaaagcct    4620
tcttttgggg gtcaacagtt ttcctatgct ttgaaacaga aaaatatgta ccaagaatct    4680
tggtttgcct tccagaaaac aaaactgcat ttcactttcc cggtgttccc cactgtatct    4740
aggcaacata gtattcatga ctatggataa actaaacacg tgacacaaac acacacaaaa    4800
gggaacccag ctctaataca ttccaactcg tatagcatgc atctgtttat tctatagtta    4860
ttaagttctt taaaatgtaa agccatgctg gaaaataata ctgctgagat acatacagaa    4920
ttactgtaac tgattacact tggtaattgt actaaagcca aacatatata tactattaaa    4980
aaggtttaca gaattttatg gtgcattacg tgggcattgt cttttttagat gcccaaatcc   5040 ttagatctgg catgttagcc cttcctccaa ttataagagg atatgaactg agttttttctt   5100 ttgttgtttg ttcttagctg taattcctat gcttctattt cagagagcca ggagagtttg    5160
atattaaagg aggttaaaac tgtgatctta tgccatgtca tcaatggcca cttaggggcc    5220
atggctgatg acacattctt atctctacag tactaatgtg ttattataga gccatgcatt    5280
ttatttctga ataagaacat atttaaacta atattcccctt acaatatgga cagtattaat   5340
ccttccaaga tgcagtattt atcaagtgaa gcatatttag cagcaaattc cattttaaca    5400
```

```
taacttagga accaataacc agggtgtttt gtggttgggg gaggcacggg gtggagtatt    5460 ctttttata tcctcaaaac aaaaaaaatc aatacttata tttc                     5504
```

<210> SEQ ID NO 2
<211> LENGTH: 909
<212> TYPE: PRT
<213> ORGANISM: Homo sapiens

<400> SEQUENCE: 2

```
Met Ala Ala Arg Pro Leu Pro Val Ser Pro Ala Arg Ala Leu Leu Leu
 1               5                  10                  15

Ala Leu Ala Gly Ala Leu Leu Ala Pro Cys Glu Ala Arg Gly Val Ser
                20                  25                  30

Leu Trp Asn Gln Gly Arg Ala Asp Glu Val Val Ser Ala Ser Val Gly
            35                  40                  45

Ser Gly Asp Leu Trp Ile Pro Val Lys Ser Phe Asp Ser Lys Asn His
        50                  55                  60

Pro Glu Val Leu Asn Ile Arg Leu Gln Arg Glu Ser Lys Glu Leu Ile
65                  70                  75                  80

Ile Asn Leu Glu Arg Asn Glu Gly Leu Ile Ala Ser Ser Phe Thr Glu
                85                  90                  95

Thr His Tyr Leu Gln Asp Gly Thr Asp Val Ser Leu Ala Arg Asn Tyr
            100                 105                 110

Thr Val Ile Leu Gly His Cys Tyr Tyr His Gly His Val Arg Gly Tyr
        115                 120                 125

Ser Asp Ser Ala Val Ser Leu Ser Thr Cys Ser Gly Leu Arg Gly Leu
    130                 135                 140

Ile Val Phe Glu Asn Glu Ser Tyr Val Leu Glu Pro Met Lys Ser Ala
145                 150                 155                 160

Thr Asn Arg Tyr Lys Leu Phe Pro Ala Lys Lys Leu Lys Ser Val Arg
                165                 170                 175

Gly Ser Cys Gly Ser His His Asn Thr Pro Asn Leu Ala Ala Lys Asn
            180                 185                 190

Val Phe Pro Pro Ser Gln Thr Trp Ala Arg Arg His Lys Arg Glu
        195                 200                 205

Thr Leu Lys Ala Thr Lys Tyr Val Glu Leu Val Ile Val Ala Asp Asn
    210                 215                 220

Arg Glu Phe Gln Arg Gln Gly Lys Asp Leu Glu Lys Val Lys Gln Arg
225                 230                 235                 240

Leu Ile Glu Ile Ala Asn His Val Asp Lys Phe Tyr Arg Pro Leu Asn
                245                 250                 255

Ile Arg Ile Val Leu Val Gly Val Glu Val Trp Asn Asp Met Asp Lys
            260                 265                 270

Cys Ser Val Ser Gln Asp Pro Phe Thr Ser Leu His Glu Phe Leu Asp
        275                 280                 285

Trp Arg Lys Met Lys Leu Leu Pro Arg Lys Ser His Asp Asn Ala Gln
    290                 295                 300

Leu Val Ser Gly Val Tyr Phe Gln Gly Thr Thr Ile Gly Met Ala Pro
305                 310                 315                 320

Ile Met Ser Met Cys Thr Ala Asp Gln Ser Gly Gly Ile Val Met Asp
                325                 330                 335

His Ser Asp Asn Pro Leu Gly Ala Ala Val Thr Leu Ala His Glu Leu
            340                 345                 350

Gly His Asn Phe Gly Met Asn His Asp Thr Leu Asp Arg Gly Cys Ser
```

```
                355                 360                 365
Cys Gln Met Ala Val Glu Lys Gly Gly Cys Ile Met Asn Ala Ser Thr
        370                 375                 380

Gly Tyr Pro Phe Pro Met Val Phe Ser Ser Cys Ser Arg Lys Asp Leu
385                 390                 395                 400

Glu Thr Ser Leu Glu Lys Gly Met Gly Val Cys Leu Phe Asn Leu Pro
                405                 410                 415

Glu Val Arg Glu Ser Phe Gly Gly Gln Lys Cys Gly Asn Arg Phe Val
            420                 425                 430

Glu Glu Gly Glu Glu Cys Asp Cys Gly Glu Pro Glu Glu Cys Met Asn
        435                 440                 445

Arg Cys Cys Asn Ala Thr Thr Cys Thr Leu Lys Pro Asp Ala Val Cys
    450                 455                 460

Ala His Gly Leu Cys Cys Glu Asp Cys Gln Leu Lys Pro Ala Gly Thr
465                 470                 475                 480

Ala Cys Arg Asp Ser Ser Asn Ser Cys Asp Leu Pro Glu Phe Cys Thr
                485                 490                 495

Gly Ala Ser Pro His Cys Pro Ala Asn Val Tyr Leu His Asp Gly His
            500                 505                 510

Ser Cys Gln Asp Val Asp Gly Tyr Cys Tyr Asn Gly Ile Cys Gln Thr
        515                 520                 525

His Glu Gln Gln Cys Val Thr Leu Trp Gly Pro Gly Ala Lys Pro Ala
    530                 535                 540

Pro Gly Ile Cys Phe Glu Arg Val Asn Ser Ala Gly Asp Pro Tyr Gly
545                 550                 555                 560

Asn Cys Gly Lys Val Ser Lys Ser Ser Phe Ala Lys Cys Glu Met Arg
                565                 570                 575

Asp Ala Lys Cys Gly Lys Ile Gln Cys Gln Gly Gly Ala Ser Arg Pro
            580                 585                 590

Val Ile Gly Thr Asn Ala Val Ser Ile Glu Thr Asn Ile Pro Leu Gln
        595                 600                 605

Gln Gly Gly Arg Ile Leu Cys Arg Gly Thr His Val Tyr Leu Gly Asp
    610                 615                 620

Asp Met Pro Asp Pro Gly Leu Val Leu Ala Gly Thr Lys Cys Ala Asp
625                 630                 635                 640

Gly Lys Ile Cys Leu Asn Arg Gln Cys Gln Asn Ile Ser Val Phe Gly
                645                 650                 655

Val His Glu Cys Ala Met Gln Cys His Gly Arg Gly Val Cys Asn Asn
            660                 665                 670

Arg Lys Asn Cys His Cys Glu Ala His Trp Ala Pro Pro Phe Cys Asp
        675                 680                 685

Lys Phe Gly Phe Gly Gly Ser Thr Asp Ser Gly Pro Ile Arg Gln Ala
    690                 695                 700

Asp Asn Gln Gly Leu Thr Ile Gly Ile Leu Val Thr Ile Leu Cys Leu
705                 710                 715                 720

Cys Ala Thr Gly Thr Ala Cys Gly Gly Gly Ala Thr Ala Thr Thr
                725                 730                 735

Cys Thr Gly Ala Thr Cys Ala Gly Cys Ala Gly Thr Cys Ala Gly
            740                 745                 750

Thr Cys Thr Cys Ala Gly Cys Ala Cys Gly Thr Gly Thr Cys Thr
        755                 760                 765

Gly Gly Thr Cys Thr Cys Ala Gly Gly Gly Gly Ala Asp Ser Tyr Pro
    770                 775                 780
```

-continued

```
Pro Lys Asp Asn Pro Arg Arg Leu Leu Gln Cys Gln Asn Val Asp Ile
785                 790                 795                 800

Ser Arg Pro Leu Asn Gly Leu Asn Val Pro Gln Pro Gln Ser Thr Gln
            805                 810                 815

Arg Val Leu Pro Pro Leu His Arg Ala Pro Arg Ala Pro Ser Val Pro
        820                 825                 830

Ala Arg Pro Leu Pro Ala Lys Pro Ala Leu Arg Gln Ala Gln Gly Thr
    835                 840                 845

Cys Lys Pro Asn Pro Pro Gln Lys Pro Leu Pro Ala Asp Pro Leu Ala
850                 855                 860

Arg Thr Thr Arg Leu Thr His Ala Leu Ala Arg Thr Pro Gly Gln Trp
865                 870                 875                 880

Glu Thr Gly Leu Arg Leu Ala Pro Leu Arg Pro Ala Pro Gln Tyr Pro
                885                 890                 895

His Gln Val Pro Arg Ser Thr His Thr Ala Tyr Ile Lys
            900                 905

<210> SEQ ID NO 3
<211> LENGTH: 3355
<212> TYPE: DNA
<213> ORGANISM: Homo sapiens

<400> SEQUENCE: 3
```

| | | | | | |
|---|---|---|---|---|---|
| gactgctggc | cgtggatcca | tttcacaggc | ctgccttctc | tcactaacgc | tcttcctagt | 60 |
| ccccgggcca | actcggacag | tttgctcatt | tattgcaacg | gtcaaggctg | gcttgtgcca | 120 |
| gaacggcgcg | cgcgcgcgca | cgcacgcaca | cacacggggg | gaaacttttt | taaaaatgaa | 180 |
| aggctagaag | agctcagcgg | cggcgcgggc | gctgcgcgag | ggctccggag | ctgactcgcc | 240 |
| gaggcaggaa | atccctccgg | tcgcgacgcc | cggcccggc | tcggcgcccg | cgtgggatgg | 300 |
| tgcagcgctc | gccgccgggc | ccgagagctg | ctgcactgaa | ggccggcgac | gatggcagcg | 360 |
| cgcccgctgc | ccgtgtcccc | cgcccgcgcc | ctcctgctcg | ccctggccgg | tgctctgctc | 420 |
| gcgcccgcg | aggcccgagg | ggtgagctta | tggaaccaag | gaagagctga | tgaagttgtc | 480 |
| agtgcctctg | ttgggagtgg | ggacctctgg | atcccagtga | agagcttcga | ctccaagaat | 540 |
| catccagaag | tgctgaatat | tcgactacaa | cgggaaagca | agaactgat | cataaatctg | 600 |
| gaaagaaatg | aaggtctcat | tgccagcagt | ttcacgaaaa | cccactatct | gcaagacggt | 660 |
| actgatgtct | ccctcgctcg | aaattacacg | gtaattctgg | gtcactgtta | ctaccatgga | 720 |
| catgtacggg | gatattctga | ttcagcagtc | agtctcagca | cgtgttctgg | tctcagggga | 780 |
| cttattgtgt | ttgaaaatga | aagctatgtc | ttagaaccaa | tgaaaagtgc | aaccaacaga | 840 |
| tacaaactct | tcccagcgaa | gaagctgaaa | agcgtccggg | gatcatgtgg | atcacatcac | 900 |
| aacacaccaa | acctcgctgc | aaagaatgtg | tttccaccac | cctctcagac | atgggcaaga | 960 |
| aggcataaaa | gagagaccct | caaggcaact | aagtatgtgg | agctggtgat | cgtggcagac | 1020 |
| aaccgagagt | tcagaggca | aggaaaagat | ctggaaaaag | ttaagcagcg | attaatagag | 1080 |
| attgctaatc | acgttgacaa | gttttacaga | ccactgaaca | ttcggatcgt | gttggtaggc | 1140 |
| gtggaagtgt | ggaatgacat | ggacaaatgc | tctgtaagtc | aggacccatt | caccagcctc | 1200 |
| catgaatttc | tggactggag | gaagatgaag | cttctacctc | gcaaatccca | tgacaatgcg | 1260 |
| cagcttgtca | gtgggttta | tttccaaggg | accaccatcg | gcatggcccc | aatcatgagc | 1320 |
| atgtgcacgg | cagaccagtc | tgggggaatt | gtcatggacc | attcagacaa | tcccttggt | 1380 |
| gcagccgtga | ccctggcaca | tgagctgggc | cacaatttcg | ggatgaatca | tgacacactg | 1440 |

```
gacaggggct gtagctgtca aatggcggtt gagaaaggag gctgcatcat gaacgcttcc   1500
accgggtacc catttcccat ggtgttcagc agttgcagca ggaaggactt ggagaccagc   1560
ctggagaaag gaatgggggt gtgcctgttt aacctgccgg aagtcaggga gtctttcggg   1620
ggccagaagt gtgggaacag atttgtggaa gaaggagagg agtgtgactg tggggagcca   1680
gaggaatgta tgaatcgctg ctgcaatgcc accacctgta ccctgaagcc ggacgctgtg   1740
tgcgcacatg ggctgctgtg tgaagactgc cagctgaagc tgcaggaac agcgtgcagg    1800
gactccagca actcctgtga cctcccagag ttctgcacag gggccagccc tcactgccca   1860
gccaacgtgt acctgcacga tgggcactca tgtcaggatg tggacggcta ctgctacaat   1920
ggcatctgcc agactcacga gcagcagtgt gtcacgctct ggggaccagg tgctaaacct   1980
gcccctggga tctgctttga gagagtcaat tctgcaggtg atccttatgg caactgtggc   2040
aaagtctcga gagttccttt gccaaatgc gagatgagag atgctaaatg tggaaaaatc    2100
cagtgtcaag gaggtgccag ccggccagtc attggtacca atgccgtttc catagaaaca   2160
aacatccccc tgcagcaagg aggccggatt ctgtgccggg ggacccacgt gtacttgggc   2220
gatgacatgc cggacccagg gcttgtgctt gcaggcacaa agtgtgcaga tggaaaaatc   2280
tgcctgaatc gtcaatgtca aaatattagt gtctttgggg ttcacgagtg tgcaatgcag   2340
tgccacggca gaggggtgtg caacaacagg aagaactgcc actgcgaggc ccactgggca   2400
cctcccttct gtgacaagtt tggctttgga ggaagcacag acagcggccc catccggcaa   2460
gcagaagcaa ggcaggaagc tgcagagtcc aacaggagc gcggccaggg ccaggagccc    2520
gtgggatcgc aggagcatgc gtctactgcc tcactgacac tcatctgagc cctcccatga   2580
catggagacc gtgaccagtg ctgctgcaga ggaggtcacg cgtccccaag gcctcctgtg   2640
actggcagca ttgactctgt ggctttgcca tcgtttccat gacaacagac acaacacagt   2700
tctcggggct caggagggga agtccagcct accaggcacg tctgcagaaa cagtgcaagg   2760
aagggcagcg acttcctggt tgagcttctg ctaaaacatg gacatgcttc agtgctgctc   2820
ctgagagagt agcaggttac cactctggca ggccccagcc ctgcagcaag gaggaagagg   2880
actcaaaagt ctggcctttc actgagcctc cacagcagtg ggggagaagc aagggttggg   2940
cccagtgtcc cctttccca gtgacacctc agccttggca gccctgatga ctggtctctg    3000
gctgcaactt aatgctctga tatggctttt agcatttatt atatgaaaat agcagggttt   3060
tagttttaa tttatcagag accctgccac ccattccatc tccatccaag caaactgaat    3120
ggcaatgaaa caaactggag aagaaggtag gagaaagggc ggtgaactct ggctcttgc    3180
tgtggacatg cgtgaccagc agtactcagg tttgagggtt tgcagaaagc cagggaaccc   3240
acagagtcac caaccettca tttaacaagt aagaatgtta aaaagtgaaa acaatgtaag   3300
agcctaactc catcccccgt ggccattact gcataaaata gagtgcattt gaaat         3355

<210> SEQ ID NO 4
<211> LENGTH: 738
<212> TYPE: PRT
<213> ORGANISM: Homo sapiens

<400> SEQUENCE: 4

Met Ala Ala Arg Pro Leu Pro Val Ser Pro Ala Arg Ala Leu Leu Leu
1               5                   10                  15

Ala Leu Ala Gly Ala Leu Leu Ala Pro Cys Glu Ala Arg Gly Val Ser
            20                  25                  30

Leu Trp Asn Gln Gly Arg Ala Asp Glu Val Val Ser Ala Ser Val Gly
        35                  40                  45
```

```
Ser Gly Asp Leu Trp Ile Pro Val Lys Ser Phe Asp Ser Lys Asn His
         50                  55                  60

Pro Glu Val Leu Asn Ile Arg Leu Gln Arg Glu Ser Lys Glu Leu Ile
 65                  70                  75                  80

Ile Asn Leu Glu Arg Asn Glu Gly Leu Ile Ala Ser Ser Phe Thr Glu
                 85                  90                  95

Thr His Tyr Leu Gln Asp Gly Thr Asp Val Ser Leu Ala Arg Asn Tyr
                100                 105                 110

Thr Val Ile Leu Gly His Cys Tyr Tyr His Gly His Val Arg Gly Tyr
                115                 120                 125

Ser Asp Ser Ala Val Ser Leu Ser Thr Cys Ser Gly Leu Arg Gly Leu
        130                 135                 140

Ile Val Phe Glu Asn Glu Ser Tyr Val Leu Glu Pro Met Lys Ser Ala
145                 150                 155                 160

Thr Asn Arg Tyr Lys Leu Phe Pro Ala Lys Lys Leu Lys Ser Val Arg
                165                 170                 175

Gly Ser Cys Gly Ser His His Asn Thr Pro Asn Leu Ala Ala Lys Asn
            180                 185                 190

Val Phe Pro Pro Ser Gln Thr Trp Ala Arg Arg His Lys Arg Glu
            195                 200                 205

Thr Leu Lys Ala Thr Lys Tyr Val Glu Leu Val Ile Val Ala Asp Asn
    210                 215                 220

Arg Glu Phe Gln Arg Gln Gly Lys Asp Leu Glu Lys Val Lys Gln Arg
225                 230                 235                 240

Leu Ile Glu Ile Ala Asn His Val Asp Lys Phe Tyr Arg Pro Leu Asn
                245                 250                 255

Ile Arg Ile Val Leu Val Gly Val Glu Val Trp Asn Asp Met Asp Lys
                260                 265                 270

Cys Ser Val Ser Gln Asp Pro Phe Thr Ser Leu His Glu Phe Leu Asp
        275                 280                 285

Trp Arg Lys Met Lys Leu Leu Pro Arg Lys Ser His Asp Asn Ala Gln
290                 295                 300

Leu Val Ser Gly Val Tyr Phe Gln Gly Thr Thr Ile Gly Met Ala Pro
305                 310                 315                 320

Ile Met Ser Met Cys Thr Ala Asp Gln Ser Gly Gly Ile Val Met Asp
                325                 330                 335

His Ser Asp Asn Pro Leu Gly Ala Ala Val Thr Leu Ala His Glu Leu
            340                 345                 350

Gly His Asn Phe Gly Met Asn His Asp Thr Leu Asp Arg Gly Cys Ser
        355                 360                 365

Cys Gln Met Ala Val Glu Lys Gly Gly Cys Ile Met Asn Ala Ser Thr
    370                 375                 380

Gly Tyr Pro Phe Pro Met Val Phe Ser Ser Cys Ser Arg Lys Asp Leu
385                 390                 395                 400

Glu Thr Ser Leu Glu Lys Gly Met Gly Val Cys Leu Phe Asn Leu Pro
                405                 410                 415

Glu Val Arg Glu Ser Phe Gly Gly Gln Lys Cys Gly Asn Arg Phe Val
            420                 425                 430

Glu Glu Gly Glu Glu Cys Asp Cys Gly Glu Pro Glu Glu Cys Met Asn
        435                 440                 445

Arg Cys Cys Asn Ala Thr Thr Cys Thr Leu Lys Pro Asp Ala Val Cys
    450                 455                 460

Ala His Gly Leu Cys Cys Glu Asp Cys Gln Leu Lys Pro Ala Gly Thr
```

```
                465                 470                 475                 480
        Ala Cys Arg Asp Ser Ser Asn Ser Cys Asp Leu Pro Glu Phe Cys Thr
                            485                 490                 495
        Gly Ala Ser Pro His Cys Pro Ala Asn Val Tyr Leu His Asp Gly His
                        500                 505                 510
        Ser Cys Gln Asp Val Asp Gly Tyr Cys Tyr Asn Gly Ile Cys Gln Thr
                    515                 520                 525
        His Glu Gln Gln Cys Val Thr Leu Trp Gly Pro Gly Ala Lys Pro Ala
                530                 535                 540
        Pro Gly Ile Cys Phe Glu Arg Val Asn Ser Ala Gly Asp Pro Tyr Gly
        545                 550                 555                 560
        Asn Cys Gly Lys Val Ser Lys Ser Ser Phe Ala Lys Cys Glu Met Arg
                            565                 570                 575
        Asp Ala Lys Cys Gly Lys Ile Gln Cys Gln Gly Gly Ala Ser Arg Pro
                        580                 585                 590
        Val Ile Gly Thr Asn Ala Val Ser Ile Glu Thr Asn Ile Pro Leu Gln
                    595                 600                 605
        Gln Gly Gly Arg Ile Leu Cys Arg Gly Thr His Val Tyr Leu Gly Asp
                610                 615                 620
        Asp Met Pro Asp Pro Gly Leu Val Leu Ala Gly Thr Lys Cys Ala Asp
        625                 630                 635                 640
        Gly Lys Ile Cys Leu Asn Arg Gln Cys Gln Asn Ile Ser Val Phe Gly
                            645                 650                 655
        Val His Glu Cys Ala Met Gln Cys His Gly Arg Gly Val Cys Asn Asn
                        660                 665                 670
        Arg Lys Asn Cys His Cys Glu Ala His Trp Ala Pro Pro Phe Cys Asp
                    675                 680                 685
        Lys Phe Gly Phe Gly Gly Ser Thr Asp Ser Gly Pro Ile Arg Gln Ala
                690                 695                 700
        Glu Ala Arg Gln Glu Ala Ala Glu Ser Asn Arg Glu Arg Gly Gln Gly
        705                 710                 715                 720
        Gln Glu Pro Val Gly Ser Gln Glu His Ala Ser Thr Ala Ser Leu Thr
                            725                 730                 735
        Leu Ile

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctccacaat atccacacca agt                                            23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgaaaaaagg tgtcggcttc tc                                             22

<210> SEQ ID NO 7
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
cccagatcca cccacaccgc ctatattaa                                     29

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttgactagat ctggttaatg                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctacgaataa tgatagcaga                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tttctatcaa gcaccgcctt                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gttgcaagtg tttaagaaat                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgctctagaa aggacagcga                                               20

<210> SEQ ID NO 13
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 13
gactgctttc caataaggcc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
acactcagag tgaattatgt                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agcacagcac agcactgacg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcttatttgt aaacagcagt                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
atactatgtt gcctagatac                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gattctactt gggatctctt                                              20

<210> SEQ ID NO 19
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 19
gctttacatt ttaaagaact                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaattatgta actgttgtca                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccacatctca taatatttag                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggtcctggcc aaggcatgag                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
taaaacactc agagtgaatt                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tggctctggc ctgagatggg                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 25
acattctgca taaattaata                                        20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttgaccccaa aagaaggctt                                        20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aaacatgctc acggctggtc                                        20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggttcacatc tgaaaatagt                                        20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctggttaatg gttcacatct                                        20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttccaaacat gctcacggct                                        20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aatcagttac agtaattctg          20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
caagattctt ggtacatatt          20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atggcatttt accttatctg          20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcccaagcta aataacctac          20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tcaagttcac taaaatacta          20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
atgccagatc taaggatttg          20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tagaataaac agatgcatgc          20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtttggctta caggtccoct                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctgtctgcaa cccaggttct                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcactttaaa gaccttgtga                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcaaagcata ggaaaactgt                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gcacacacct tagtttttca                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agcaggatat ttcaagttca                                              20

```
<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgttgcctag atacagtggg                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cattaaccag atctagtcaa                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tctgctatca ttattcgtag                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aaggcggtgc ttgatagaaa                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
atttcttaaa cacttgcaac                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tcgctgtcct ttctagagca                                              20

<210> SEQ ID NO 50
<211> LENGTH: 20
```

-continued

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggccttattg gaaagcagtc                                           20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
acataattca ctctgagtgt                                           20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cgtcagtgct gtgctgtgct                                           20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
actgctgttt acaaataaga                                           20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtatctaggc aacatagtat                                           20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aagagatccc aagtagaatc                                           20

<210> SEQ ID NO 56
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 56 agttcttaa aatgtaaagc                                                    20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tgacaacagt tacataattc                                                   20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ctcatgcctt ggccaggacc                                                   20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
aattcactct gagtgtttta                                                   20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cccatctcag gccagagcca                                                   20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tattaattta tgcagaatgt                                                   20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 62
aagccttctt ttggggtcaa                                              20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gaccagccgt gagcatgttt                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
actattttca gatgtgaacc                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
agatgtgaac cattaaccag                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
agccgtgagc atgtttggaa                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cagaattact gtaactgatt                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 68
aatatgtacc aagaatcttg                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cagataaggt aaaatgccat                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gtaggttatt tagcttggga                                              20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caaatcctta gatctggcat                                              20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gcatgcatct gtttattcta                                              20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aggggacctg taagccaaac                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
```

-continued

```
agaacctggg ttgcagacag                                              20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tcacaaggtc tttaaagtga                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
acagttttcc tatgctttga                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tgaacttgaa atatcctgct                                              20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cccactgtat ctaggcaaca                                              20
```